US012526589B2

(12) United States Patent
Pindor et al.

(10) Patent No.: US 12,526,589 B2
(45) Date of Patent: Jan. 13, 2026

(54) METHOD AND SYSTEM OF AUDIO PROCESSING USING COCHLEAR-SIMULATING SPIKE DATA

(71) Applicant: Intel Corporation, Santa Clara, CA (US)

(72) Inventors: Lukasz Pindor, Gdansk (PL); Daniel David Ben-Dayan Rubin, Jerusalem (IL); Adam Kupryjanow, Gdansk (PL)

(73) Assignee: Intel Corporation, Santa Clara, CA (US)

( * ) Notice: Subject to any disclaimer, the term of this patent is extended or adjusted under 35 U.S.C. 154(b) by 673 days.

(21) Appl. No.: 17/861,784

(22) Filed: Jul. 11, 2022

(65) Prior Publication Data

US 2022/0408201 A1 Dec. 22, 2022

(51) Int. Cl.

| | |
|---|---|
| ***G10L 25/78*** | (2013.01) |
| ***A61N 1/36*** | (2006.01) |
| ***H04R 25/00*** | (2006.01) |

(52) U.S. Cl.

CPC ....... *H04R 25/507* (2013.01); *A61N 1/36038* (2017.08); *H04R 2225/67* (2013.01)

(58) Field of Classification Search

CPC .... H04R 25/507; H04R 2225/67; H04R 3/00; H04R 2499/11; A61N 1/36038; G10L 25/78; G10L 17/02

USPC .................................................... 381/61, 312

See application file for complete search history.

(56) References Cited

U.S. PATENT DOCUMENTS

2011/0125508 A1* 5/2011 Kelly .................... H04H 20/31 704/502

* cited by examiner

*Primary Examiner* — George C Monikang

(74) *Attorney, Agent, or Firm* — Akona IP PC

(57) ABSTRACT

A method and system of audio processing encodes cochlear-simulating spike data into spectrogram data.

25 Claims, 11 Drawing Sheets

Array Au

800

| | S1 | S2 | S3 | S4 | S5 | S6 | S7 | S8 | S9 | S10 | S11 | S12 | ... | $S_C$ |
|---|---|---|---|---|---|---|---|---|---|---|---|---|---|---|
| C1 | 1 | 1 | 0 | 0 | 0 | 0 | 0 | 1 | 0 | 1 | 1 | 0 | ... | 0 |
| C2 | 1 | 1 | 0 | 1 | 0 | 1 | 0 | 0 | 1 | 1 | 0 | 0 | | |
| C3 | 1 | 0 | 1 | 0 | 1 | 1 | 1 | 1 | 0 | 0 | 1 | 0 | | |
| C4 | 0 | 1 | 0 | 1 | 1 | 1 | 1 | 1 | 0 | 1 | 1 | 0 | | |
| ⋮ | | | | | | | | | | | | | | ⋮ |
| C | 1 | | | | | | | | | | | | ... | |

Array Ag

850

| | f1 | f2 | f3 | f4 | f5 |
|---|---|---|---|---|---|
| C1 | 2 | 0 | 1 | 2 | 2 |
| C2 | 3 | 2 | 1 | 2 | 2 |
| C3 | 2 | 3 | 4 | 2 | 1 |
| C4 | 2 | 3 | 4 | 3 | 2 |
| ⋮ | | | | | |
| C | 1 | | | | |

1000

1100

1200

1300

METHOD AND SYSTEM OF AUDIO PROCESSING USING COCHLEAR-SIMULATING SPIKE DATA

BACKGROUND

Audio processing and analysis applications typically use artificial neural networks (ANNs) to provide highly accurate audio applications. Such applications include automatic speech recognition and particularly wake-on-voice (WoV) applications systems that are "always on" systems that awaken a device or application upon hearing a person speak certain keywords, and that are always consuming power to monitor for the keywords. This is typical on small internet-of-things (IoT) devices or other mobile devices such as a smart phone that have relatively small processing and memory capacities. The ANNs, however, often consume relatively large computational loads and memory capacities, making ANNs inefficient or difficult to use for small computing devices.

Instead of the ANNs, attempts have been made to use spiking neural networks (SNNs) that receive input audio data in the form of spikes rather than continuous time-domain audio signal data. Some SNNs receive their input spikes from a cochlea model that imitates the human (or animal) auditory cochlear frequency detection of input waveform audio signals generates the spike, although other models, such as a Pan model are used. The SNNs have a much more compressed, smaller computational load and memory requirements, but still do not provide sufficient accuracy when the SNNs are used to classify audio data and then used to reconstruct the time domain audio signal waveform to be used for a variety of downstream audio processing applications.

DESCRIPTION OF THE FIGURES

The material described herein is illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. In the figures.

DETAILED DESCRIPTION

Figure 1:
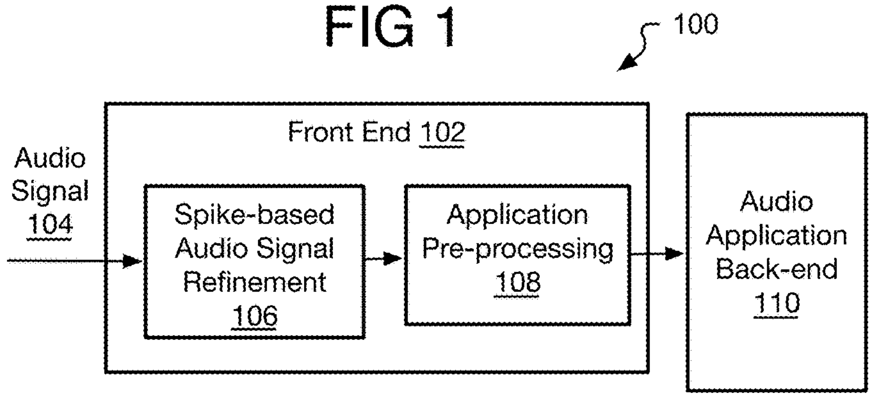
FIG. 1 is a schematic diagram of an audio processing device according to at least one of the implementations herein.

One or more implementations are now described with reference to the enclosed figures. While specific configurations and arrangements are discussed, it should be understood that this is performed for illustrative purposes only. Persons skilled in the relevant art will recognize that other configurations and arrangements may be employed without departing from the spirit and scope of the description. It will be apparent to those skilled in the relevant art that techniques and/or arrangements described herein may also be employed in a variety of other systems and applications other than what is described herein.

While the following description sets forth various implementations that may be manifested in architectures such as system-on-a-chip (SoC) architectures for example, implementation of the techniques and/or arrangements described herein are not restricted to particular architectures and/or computing systems and may be implemented by any architecture and/or computing system for similar purposes. For instance, various architectures employing, for example, multiple integrated circuit (IC) chips and/or packages, and/or various computing devices and/or consumer electronic (CE) devices such as computing systems that have or receive acoustic signals from one or more microphones, but also may include laptop or desktop computers, tablets, mobile devices such as smart phones, smart speakers, smart watches, and/or smart headphones or head mounted displays (HMDs), internet of things (IoT) devices, video game panels or consoles, virtual, augmented, or mixed reality systems, high or low definition audio systems, surround sound or neural surround home theatres, television set top boxes, on-board vehicle systems, dictation machines, hearing aids, security and environment control systems for buildings, and so forth, may implement the techniques and/or arrangements described herein. Further, while the following description may set forth numerous specific details such as logic implementations, types and interrelationships of system components, logic partitioning/integration choices, and so forth, claimed subject matter may be practiced without such specific details. In other instances, some material such as, for example, control structures and full software instruction sequences, may not be shown in detail in order not to obscure the material disclosed herein. The material disclosed herein may be implemented in hardware, firmware, software, or any combination thereof. The terms audio and acoustic are used interchangeably herein.

The material disclosed herein also may be implemented as instructions stored on a machine-readable medium or memory, which may be read and executed by one or more processors. A machine-readable medium may include any medium and/or mechanism for storing or transmitting information in a form readable by a machine (for example, a computing device). For example, a machine-readable medium may include read-only memory (ROM); random access memory (RAM); magnetic disk storage media; optical storage media; flash memory devices; electrical, optical, acoustical, or other forms of propagated signals (e.g., carrier waves, infrared signals, digital signals, and so forth), and others. In another form, a non-transitory article, such as a non-transitory computer readable medium, may be used with any of the examples mentioned above or other examples except that it does not include a transitory signal per se. It does include those elements other than a signal per se that may hold data temporarily in a "transitory" fashion such as RAM and so forth.

References in the specification to "one implementation", "an implementation", "an example implementation", and so forth, indicate that the implementation described may include a particular feature, structure, or characteristic, but every implementation may not necessarily include the particular feature, structure, or characteristic. Moreover, such phrases are not necessarily referring to the same implementation. Further, when a particular feature, structure, or characteristic is described in connection with an implementation, it is submitted that it is within the knowledge of one skilled in the art to affect such feature, structure, or characteristic in connection with other implementations whether or not explicitly described herein.

Systems, articles, media, and methods of audio processing using cochlear-simulating spike data are described herein.

As mentioned, SNNs receive an audio signal represented by audio data formed of spikes (binary impulses over time). The spikes are generated by using a cochlea model (or "artificial cochlea") to convert an audio signal into the spikes, or in other words, spike data sufficient to form a cochleogram (or just cochleogram data). The cochlea model extracts temporal signatures corresponding to each characteristic frequency over tonotopic projections similar to the operation of a human or animal cochlear filter bank. These are early audio processing operations applied to an auditory signal are highly non-linear and follow inner ear neurophysiology. The cochleogram data is then used as the input for the SNN.

The SNN then processes the spikes from the cochlea model and simulates a reduced brain function such as neurons' temporal dynamics to provide output spikes. SNNs are usually entirely spike based so that both the input and output to the SNN are spikes. The audio systems that are based on SNNs use the output spikes for classification tasks, such as with wake-up phrase detection for WoV, and may use the output spikes directly or may reconstruct the waveform audio signal data for further processing. This process usually omits much pre-processing that increases audio signal quality such as with noise suppression or dynamic noise suppression (DNS), and other such pre-processing tasks.

The inverse conversion of the cochleogram data (or spikes) back to an audio signal with a single amplitude value over time forming a waveform is not trivial. It usually depends on several detailed assumptions of the generating cochlea or cochlear model, such as how well the model represents non-linearities, the number of filters it uses, the model's binarization process, and whether or not it was arranged with reversibility in mind. The conventional systems that convert spikes back to the time domain audio signal typically cannot provide high quality audio signals with highly accurate frequencies because conventional systems often attempt to reconstruct both a magnitude spectrum and phase, the input spikes are not preprocessed (such as by downsampling, spike grouping) before fitting the network, and the conventional network architecture is not properly arranged.

By extension, many of the conventional systems decode audio signals into spikes, modify the spikes using an SNN, and then encode the spikes to reconstruct the audio signals while using the same convolving audio kernels for both decoding and encoding except in reverse order for the encoding. This lack of precise and/or customized audio processing operation kernels for the encoding reconstruction versus the decoding further reduces the quality of the resulting audio signals while using the SNNs.

Also, a few relevant audio processing methods were developed to reconstruct audio signals by imitating auditory nerve activity. One known two-stage approach proposes reconstruction of spectrogram audio signal data from spikes generated by a cochlea model by using a multi-layer perceptron (MLP or in other words, supervised learning of binary classifiers) for low frequency reconstruction (below 2 kHz), and an iterative method for audio signal reconstruction for high frequencies recovery. However, this approach results in a reconstructed audio signal that has poor quality.

Another known audio signal reconstruction technique proposes a biological auditory encoding (BAE) tempotron that uses a full pipeline with a decoder to convert an input audio signal to spikes, and an encoder that performs the reverse conversion to reconstruct the audio signal directly from the spikes. The tempotron is a supervised synaptic learning algorithm which is applied when the audio signal information is encoded in spatio-temporal spiking patterns. This is an advancement of the perceptron, which does not incorporate a spike timing framework. This solution defines an invertible auditory front-end. The BAE-tempotron enables a high accuracy speech recognition rate when combined with SNNs. This technique, however, only generates graded spikes (not binary) such that floating point numbers are generated. This therefore, cannot be used with SNN networks. Thus, this method cannot be easily used with various cochlea models (and could not be used with real auditory input from biological auditory nerves for example).

To resolve these issues, a system and method disclosed herein converts or encodes cochleogram data such as spikes directly into spectrogram data. Spikes refer to the spiking response of a biological or artificial cochlea to some incoming sound and specifically to spike timing along a sample sequence of an audio signal for example, and spectrogram data includes the audio signal's sound magnitude spectrum. The convertor may be referred to as a cochleogram encoder since it encodes spikes (cochleogram data) into a different domain, i.e., a magnitude spectrum. The encoder may be arranged to receive spikes in many different formats and is not limited to receiving spikes (or cochleogram data) from a specific cochlea model.

The encoder may have a neural network (NN) with topology to convert spike data into magnitude spectrum data. This may be repeated for a sequence of frames input to the neural network where each frame represents one or more sample times. The cochleogram data is treated here as an unknown transformation by the hidden layers of a deep neural network, which by one form, may be a convolutional neural network (CNN). The NN roughly simulates the operation of a fast Fourier transform (FFT) in that the NN uses the spikes to determine magnitudes for specific channels or frequency components represented by the spikes. The encoder NN is not an SNN since the encoder NN here provides output in the form of spectrogram data rather than modified spikes. In other words, a magnitude spectrum is provided by the output nodes of the encoder NN such that each sample time point or frame that is input may be provided a magnitude for each frequency component at that time point, thereby providing audio data that is sufficient to generate a spectrogram. This is in contrast to direct conversion to a time domain audio signal with a waveform with a single varying amplitude over time.

Thus, it has been determined that the neural network here generate magnitude values of an audio signal by inputting only spike timing for multiple channels or frequency components with no magnitude data at the input. The magnitude values output from the neural network may not be precise and may be approximations, but the values are sufficiently close to the original magnitude values to raise the accuracy (or quality) of a reconstructed audio signal when the output magnitude spectrums are converted into a time domain audio signal after being output from the encoder NN. It is believed this works because the cochlea model, simulating biological ear operations, outputs a spike timing pattern that can be graphically similar to a spectrogram of the same audio signal. In other words, the density and pattern of the spikes on a cochleogram is sufficiently similar to, and indicative of, the magnitude patterns on a spectrogram so that a neural network can recognize these similarities to estimate the magnitudes. Therefore, the present methods provide a high quality reconstructed audio signal of many different original audio signal types, whether clean or noisy.

In order to reduce the computational load of the encoder in one alternative, the spikes may be downsampled (or compressed) before inputting the spikes into the encoder NN. This may be performed by a windowing operation that sums the spikes in a time window of the generated spike trains from the cochlea model. The window sums a count of spikes in a number of samples (or sample times) covered by the window along a whole sequence of sample times. Thereafter, the counts for each window, and in turn for each channel (or frequency component as provided by the cochlea model), are binarized to indicate whether at least one spike exists during a certain time window, and for each channel being provided. The result is a binarized spike group map that can be input to the encoder NN.

In order to further compress the spike data, and whether or not downsampling has been performed, spike grouping may be performed by using summing similar to that performed by the downsampling. For spike grouping, the series of samples (or sample times) being summed are referred to as frames and are summed for individual channels. When no previous downsampling has occurred, the actual spike indicators of the samples (0 or 1 that indicate if a spike is present) is summed in each frame. When downsampling has already occurred, spike group indicators on a spike group map are summed where each spike group indicator already may represent multiple consecutive samples (or consecutive sample times). The spike group indicator indicates at least one spike exists in a sequence of consecutive samples. The sums are then maintained in a grouped array where channels form the rows and individual frames each have a column on the grouped array (or vice-versa). In order to significantly increase accuracy of the reconstructed audio signal data, a more continuous representation of the original audio signal is achieved by overlapping the frames in an initial array (or ungrouped array) to form the frame columns in the grouped array for the spike grouping as well. The grouped array is input to the encoder NN. The result is a system and method that enables high quality audio signal reconstruction that is highly compressed (relatively low amount of computations) with relatively low power consumption.

Thus, the proposed solution of a cochlear encoder provides a high-quality audio signal for general or application-specific pre-processing operations such as dynamic noise suppression (DNS) or any denoising, acoustic echo cancelation (AEC), automatic gain control (AGC), blind source separation (BSS), dereverberation (DRV), and so forth.

The disclosed cochleogram encoder also increases the accuracy and performance of end applications that may use the output reconstructed audio signal whether directly or after pre-processing, such as automatic speech recognition (ASR), wake on voice (WoV), or other keyword spotting applications, speaker recognition (SR), angle of arrival (AOA) detection, and so forth. It also will be appreciated that a spike-to-spectrogram data encoder may be used to perform conversion of impulses from a human or animal brain to assist with auditory nerve activity analysis. In this case, the spikes can be provided from a cochlea model physically inter-connected to a being's auditory nerves to form the spikes and may include a brain computer interface via auditory canal surgery, as one possible example. In this case, a cochlea model receives audio data via such biologically based interconnections rather than microphones, and may merely arrange the spike data rather than convert the spike data from waveform audio signals itself.

Referring to FIG. 1, an audio processing system or device 100 comprises components of many different audio processing systems including for ASR, WoV, KWD, as well as SR and/or speaker identification, AOA detection, and so forth. System 100 may have a front end 102 that receives a raw audio signal 104 in a time domain and with a waveform such as from an audio capture device such as one or more microphones. Otherwise, the audio signal could be from a biological interconnection and may already be spike-related. The front end 102 may be used to refine or clean the audio signal before providing the audio signal to the audio application back-end 110. The front end 102 may have a spike-based audio signal refinement unit 106 that performs the audio signal reconstruction disclosed herein before providing the high-quality reconstructed audio signal to an application pre-processing unit 108 that further refines the audio signal by performing general pre-processing such as denoising, or pre-processing specific to an application, such as refinements that are particularly useful specifically for an end application such as WoV, and so forth, including signal conditioning, sampling rate conversion, signal equalization, and/or pre-emphasis filtration to flatten the signal, to name a few examples. The pre-processing unit 108 also may or may not divide the acoustic signal into frames.

The audio application back end 110 has any unit that is specific to a particular audio end application (even though the application itself may have its own internal acoustic front and back ends). Thus, for WoV or ASR, these may include any one or more units for everything from voice activity detection (VAD), feature extraction, acoustic scoring, decoding (whether by weighted finite state transducers (WFSTs) or other structure), language interpretation, and so forth. Any of these more initial (VAD, feature extraction, etc.) may be considered part of the pre-processing unit 108 as well.

Figure 2:
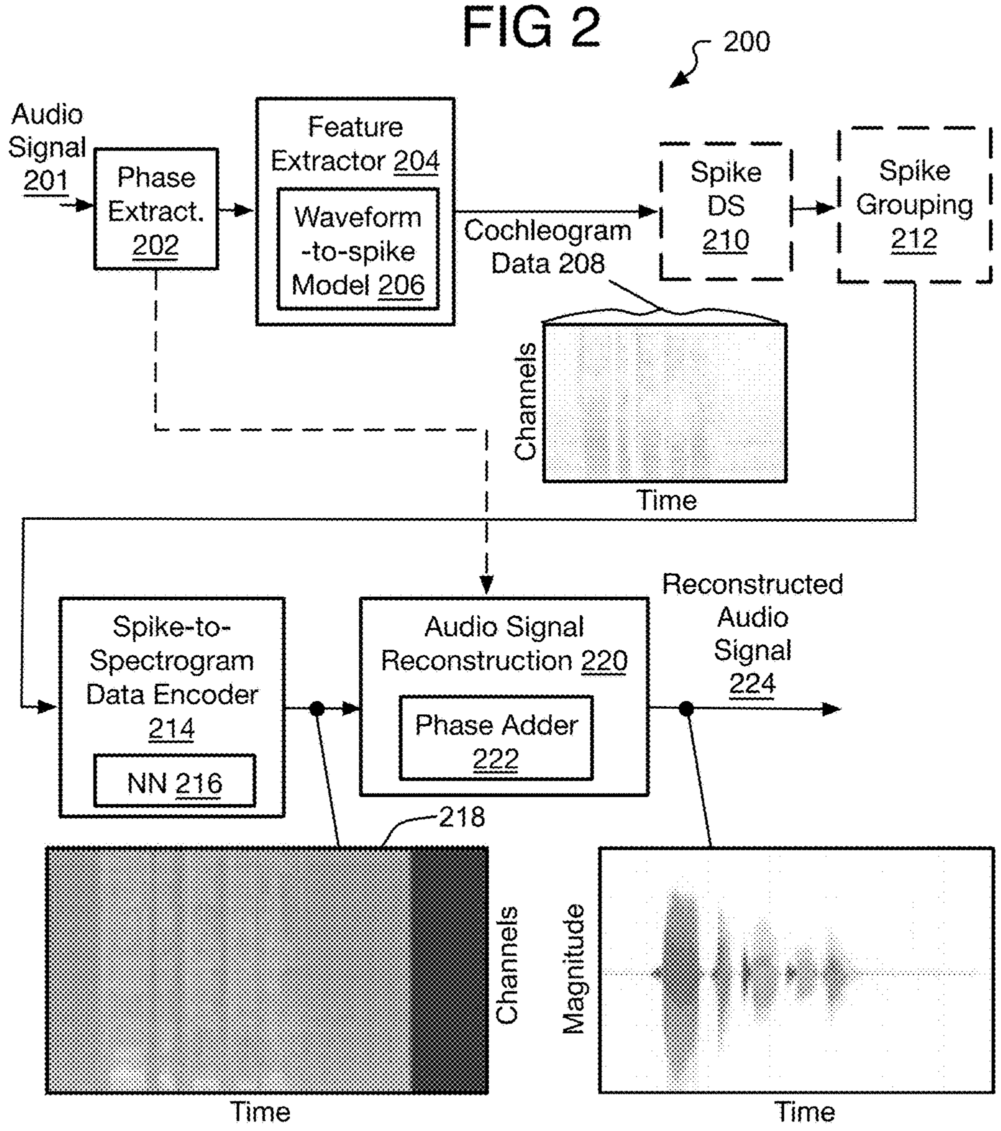
FIG. 2 is a schematic diagram of a spike-based audio signal generator according to at least one of the implementations herein.

Referring to FIG. 2, a spike-based audio signal refinement unit 200 is shown and is the same or similar to the spike-based audio signal refinement unit 106 described above. The refinement unit 200 has a phase extractor 202 and a feature extractor 204 with a waveform-to-spike model 206. The model 206 may be a cochlea model that generates cochleogram data 208 in the form of spike timing over multiple channels (or frequency components). By one form, the cochleogram data may be sufficient to form a cochleogram as shown where channels are along the y-axis and time is along the x-axis. The filled in spaces on the cochleogram shows the density of the spikes at the channels over time. The formation of the cochleogram is for explanatory purposes only and need not actually be formed during the process.

The cochleogram data 208 optionally may be provided to a spike downsampling unit 210 and, when provided, a spike grouping unit 212 whether or not the downsampling unit 210 is provided. A spike-to-spectrogram data (or spike-to-magnitude) convertor or encoder 214 is provided with a neural network (NN) 216 to encode the spike data into magnitude spectrums 218 shown on a spectrogram. The spectrogram graphs frequency by time where different colors on the graph are magnitudes so that each time point has a magnitude spectrum. As described in detail herein, the encoder 214, and in turn neural network 216, may receive a version of spike data such as spikes counts or spike group indicators over a sequence of samples or sample times generated at a certain sample rate. The spike data is provided per frequency (or channel) without magnitude values (or versions thereof) as the inputs to the encoder and encoder NN, while the outputs of the encoder NN are magnitude spectrums. The details are provided below.

The magnitude spectrums 218 (shown on the spectrogram) then may be provided to an audio signal reconstruction unit 220 to use the spectrums to generate a reconstructed time-domain audio signal 224 with a varying amplitude (or magnitude) that forms a waveform for the audio signal. The reconstruction is performed by using a phase adder 222 that receives angular spectrum components from the phase extractor 202 since spike or cochleogram data has poor phase information. The reconstructed audio signal 224 then can be pre-processed and otherwise used by audio end applications. An end application merely refers to an application that uses audio signal data for another purpose such as speech recognition (rather than merely constructing or refining an audio signal), and is not necessarily the last application to use the audio data or signal.

Figure 3:
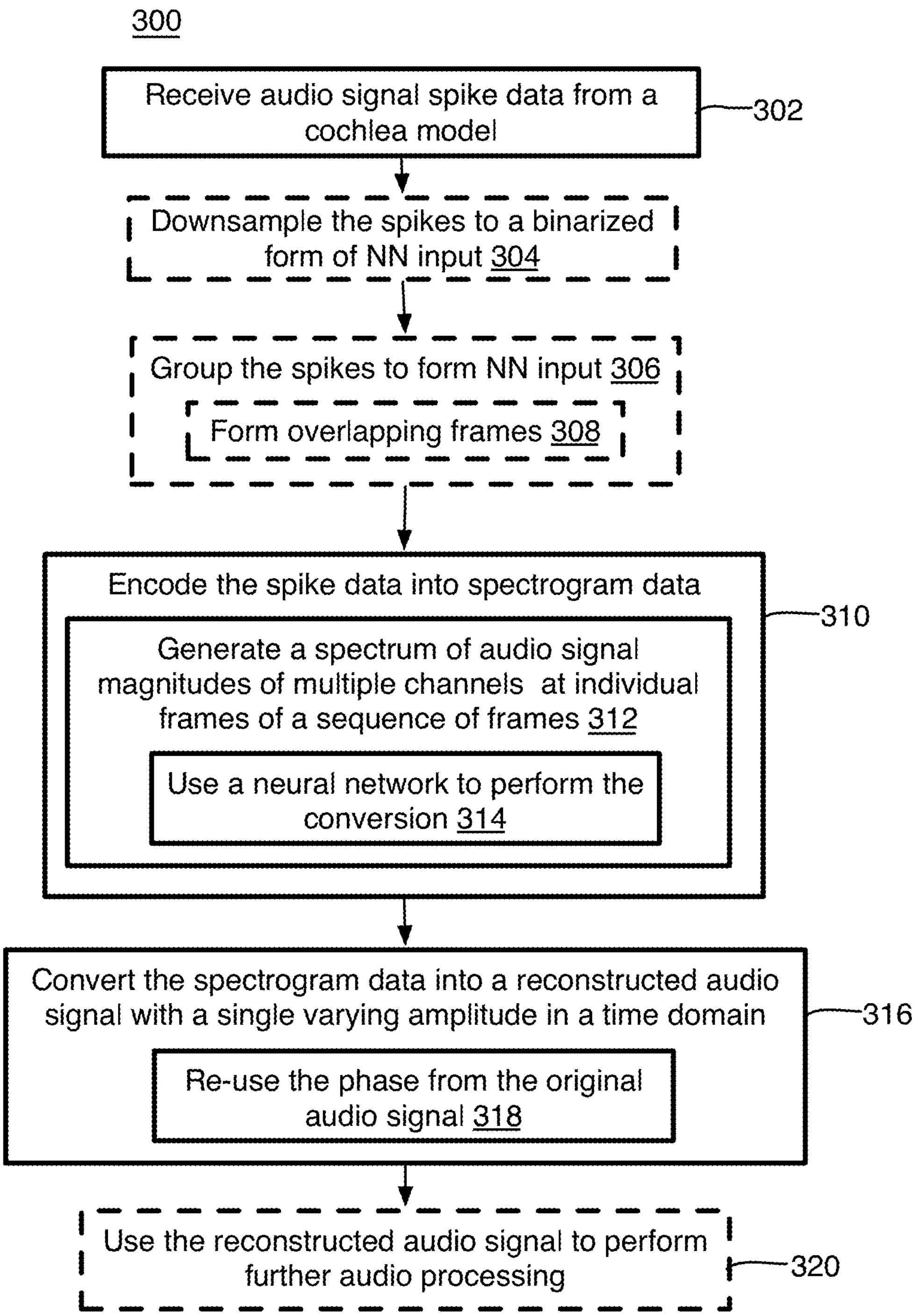
FIG. 3 is a flow chart of an example method of audio processing dynamic noise suppression for audio processing according to at least one of the implementations herein.
Figure 4:
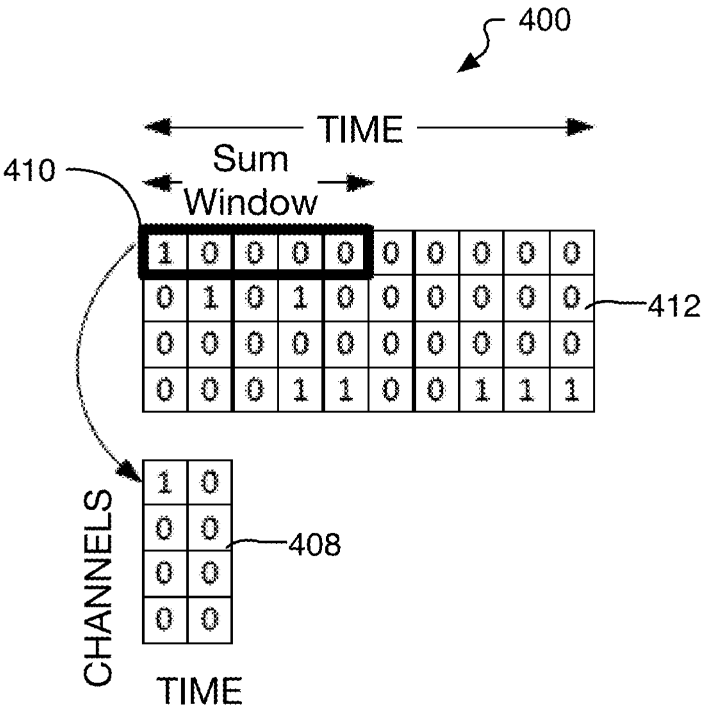
FIGS. 4-7 are schematic diagrams showing a downsampling and binarization process according to at least one of the implementations herein.
Figure 5:
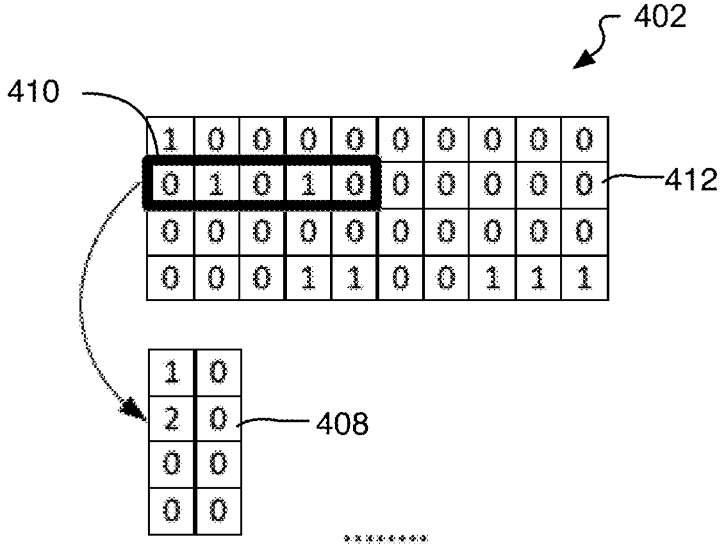
Figure 6:
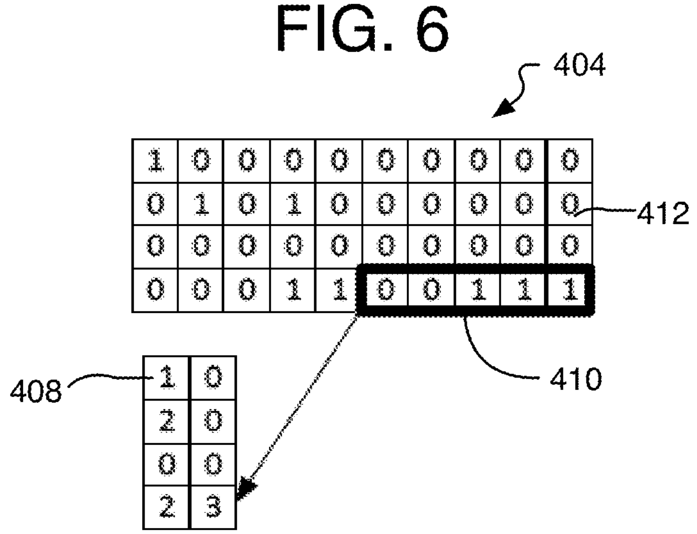

Referring to FIG. 3, an example process 300 provides a computer-implemented method of audio processing with cochlear-simulating spike data according to at least one the implementations herein. Process 300 may include one or more operations, functions or actions as illustrated by one or more of operations 302 to 320 numbered evenly. By way of non-limiting example, process 300 may be described herein with reference to example acoustic processing devices or systems of any of FIGS. 1-2 and 14-16, and where relevant.

Process 300 can be considered to perform three different stages. First, process 300 performs data preparation that may include waveform audio signal to spike conversion, and then downsampling and spike grouping when desired (this also may include extracting phase from the original audio signal wave as described below). Next, spikes-to-spectrum magnitude encoding may be performed, and then signal reconstruction that uses the magnitude spectrums to construct a time domain audio signal. Preliminarily, the audio signal may be generated by one or more analog or digital microphones or other audio device that captures acoustic waves and converts the waves into an audio signal. The audio signal may be converted to a digital signal when needed, and then either stored in memory and provided to the audio processing system 100, streamed directly to the audio processing system, or otherwise transmitted wirelessly or via wire to the audio processing system. There is no limit to the type, purpose, or condition of the audio signal (where condition refers to how much noise is in the audio signal, by one example) as long as the audio signal is provided in a form that can be converted into spikes, such as in a time domain form where a single signal has a single varying amplitude to generate a waveform for the audio signal. By another approach, spike-related data may be provided from a biologically inter-connected apparatus that provides or represents a version of real auditory nerve signals.

Another preliminary operation may be to detect and transmit the angular spectrum of the input or original audio signal before it is converted into spikes. This is performed to be able to reinstate the phase of a given frequency while reconstructing the audio signal at the output of the spike-based audio signal refinement unit 200 for example. The phase detection may simply be determined by running the input audio signal through a fast Fourier transform (FFT) to determine and output the inter-frequency phases. A timing pulse or other indicator of each frequency at certain sample times along a sample sequence may relate the phases (or cycle) to a subsequent phase, and may be transmitted for re-stablishing the phase later at the reconstructed audio signal as described below.

To begin data preparation, process 300 may include "receive audio signal data comprising spike data from a cochlea model" 302. The waveform time domain audio signal to spike conversion may be performed by using a cochlea model. Any waveform to spike conversion algorithm can be utilized here as long as the information representation is robustly encoded. In the spike domain, the spike timing has a very sparse representation of the original audio signal. Thus, in this representation, the audio signal should be highly oversampled for high accuracy. By one form, the cochlea model may have a very high sampling rate at about 100 kHz when the typical audio signals used in noise suppression may be sampled at a much lower 16 kHz. The sampling rate may be a suggested parameter of the cochlea model itself. As explained below, downsampling may be used to reduce the sampling rate to 1 kHz.

While just about any spike generating cochlea model may be used, the methods herein were tested on a Zilany cochlea model (Zilany, I. C., et al., Updated parameters and expanded simulation options for a model of the auditory periphery, The Journal of the Acoustical Society of America, 135(1):283-286 (January 2014)). The Zilany cochlea model uses a cochlear-simulating filter bank that simulates biological auditory frequency detection in a brain. This model uses power-law (or gamma) compression techniques. The output of a gamma-tone filter can be regarded as a measurement of basilar membrane displacement.

The Zilany cochlea model decomposes an audio signal into channels (or frequency components). The channels are defined by the Zilany model as a number of band-pass-like filters which correspond to ascending tonotopic cochlear sections from high frequency (HF) to low frequency (LF). Each filter may have a number of fibers in the Zilany model, which correspond to slightly different spiking neurons on that tonotopic filter. Specifically, fibers are defined in Zilany as simulating auditory nerve fibers. Three types of fibers are implemented including high-spontaneous rate (HSR) fiber per frequency, medium-spontaneous rate (MSR) fiber per frequency, and low-spontaneous rate (LSR) fiber per frequency. A filter can have any one or combination of these types of fibers. For the system and method disclosed herein, the channels are considered to use just the LSR fibers. Each different combination of filter and fiber is a different channel.

A waveform-to-spike cochlea model can produce any number of channels, and the encoder described herein can work with any number of channels. Herein, however, the present system and method was tested with 16 filters each with 16 channels for a total of 256 channels because it gave the best quality results so far and fits well with the FFT size for reconstructing the audio signal used herein. Moreover, 256 channels provides a sufficiently robust result performed by a reduced computational load. It was found that generally, the more channels, the greater the accuracy of the system (the higher the quality of the reconstructed audio signal) up until 256 channels where over-presentation could occur with more than 256 channels. The arrangement with 16 channels and 16 fibers was found to be sufficiently robust. Other possible variations with the Zilany model that could be used include any combination of 16, 32, 64, 128, and 256 channels with 1, 2, 4, 8, or 16 fibers each. As mentioned, other cochlea models may have different channel arrangements.

The channel (or frequency) range may cover the entire auditory spectrum of human hearing from 20 Hz to 20 kHz, but could be set for other smaller or larger ranges, and may include the hearing ranges of other beings (beyond human hearing range) such as at 0 to 24 kHz, or even behind auditory ranges.

It also will be appreciated that while non-biological cochlea models mentioned above, such as the Zilany model, simulates the entire auditory process from receiving ambient acoustic waves at microphones to generation of spikes, instead biological cochlea models may be used that receive spike-related data from real physical auditory nerve signals from a being's brain rather than microphones, and the biological cochlea model converts such biologically-based spike related data into channel spike data as described above with the non-biological cochlea models.

The non-biological cochlea model, such as the Zilany model, generates spiking data by converting an audio signal waveform into a multichannel spike train (a spike train for each channel). Thus, the output can be in a form of a vector of spike times relative to a reference time for each channel. Alternatively, the output can be a binary vector of zeros and ones so that when a spike occurs, a one exists on a sample. This latter case assumes a sampling frequency that can distinguish two separate spikes and not lose information during reconstruction of the audio signal. By one form, a 1 kHz sampling rate could be used for the output of the cochlea model for this alternative so that the output does not need to be downsampled.

By another format, the cochlea model output may be a timestamp of a spike and a channel number of the spike occurring at the time stamp. When a timestamp is not produced at a certain interval or period, this can be interpreted as a period with zeros or no spikes on any channel. So, for a random example, a time stamp of 1 (at 1 second) may have spikes in channels, e.g., channels 1, 4, and 150, while no time stamp may be provided at times 1-5 seconds where no spikes exist.

Also in some cochlea models, such as the Zilany model used herein, the magnitudes are still usually encoded in the local frequency of each spike train. By one alternative, these magnitudes, however, are not used for the subsequent operations, whether for downsampling, spike grouping, or encoding of spikes into magnitude spectrums. These magnitudes are dropped instead.

At this stage, the output of the cochlea model could be collected and arranged to either be direct input into the spike-to-spectrogram data encoder or to be used for further processing before being input to the encoder. The collecting and arranging of the spike data may involve arranging the spike data, or treating the spike data as if so arranged, in an initial input array $A_{cm}$ from the cochlea model where each row is a different channel and each column is a different sample or sample time in order of a temporal sequence of the samples at a sample rate. Each location on the array may have a one to indicate a spike or 0 when no spike exists. Then when used as direct input, the input array $A_{cm}$ may be loaded into the encoder NN, and specifically into an internal input buffer of the encoder NN. Such a buffer may receive one column at a time but should hold at least a number of columns of the input array $A_{CM}$ to be used together in convolutional computations.

For an alternative approach with better performance, process 300 optionally may include "downsample the spikes to a binarized form of NN input" 304, and in order to further compress the spike data to be encoded when desired to increase performance by reducing the computational load. When an audio signal-to-spike conversion algorithms used by cochlea models oversamples the audio signal prior to conversion, and by one form up to 100 kHz as mentioned above, that simulates a biological auditory frequency. Given the data and compute overload used by the cochlea model in this present example, a time-binned downsampling block may be used. This is performed to downsample the cochleogram data with a relatively high biological sampling frequency of 100 kHz down to a more manageable sampling frequency of 1 kHz.

The downsampling here does not compress the channels, and each channel provided by the cochlea model is still maintained separately from the other channels during downsampling operations. By this example approach, the downsampling or compression is temporal only. Depending on a targeted sampling rate, any size summing window may be used on the cochleogram data array $A_{cm}$. Thus, if it is desirable to downsample cochleogram data from 100 kHz to a minimum of 1 kHz to effectively reduce the number of samples 100 times, the summing window should be 1/1000 seconds. The downsampling can be shown mathematically by an algorithm that operates a moving summing window without overlap and returns a binarized value o( ) for each channel:

$$o(t') = \Theta\left(\sum_{s=1..T} x(t'-s)\right) \tag{1}$$

where t'={T, 2T, . . . } is the window position (window width over multiple sample columns) on a single row for a single channel, T is the window length in number of samples, Θ( ) is the Heaviside function, and where x( ) is the spike indicator from the cochleogram data within window position t' at sample (or column) position s within the window.

Referring to FIGS. 4-7 to illustrate the downsampling operation, a sampling block 412 is shown at a first stage 400 and may be part of an initial array $A_{CM}$ as described above where each row provides spike data (a spike indicator) for a separate channel and each column provides a different sample (or sample time) over a sequence of the temporal samples. There may be up to C channels, here being set at 256 channels as explained above but could be any desired amount of channels. The sample block 412 here shows 4 rows (channels) and 10 columns (sample times) just for simplicity. It will be understood that the actual operation of the downsampling may be performed over the entire array $A_{CM}$ without dividing the array into blocks.

In this example, a moving summing window 410 is shown with a sample size of T=5. Stage 400 shows the window 410 in a first upper left location on the block 412. The five samples in the window are summed to generate a count of spikes over the five sample times covered by the window, here shown as 1. The sum is then placed in a spike count table or map 408 that has one space for each channel, here by row, and a different window location for each column. In this example, the window locations do not overlap on the array $A_{CM}$ 412 although such overlap could be used, as shown below with spike grouping operations.

In this example, a stage 402 (FIG. 5) shows the window 410 moved downward to the next row, and in turn channel, but still extending over the same five sample times (or columns). The second window sum is then placed in the next lower space on the spike count map 408, here being a spike sum of 2. Stage 404 (FIG. 6) shows the window 410 has already moved in a "window width" column by column manner down the four rows of block 412, until the window 410 is shown at a last window location in block 412. This results in a filled spike count map 408 with a single spike count sum for each window position on block 412. This may be repeated for each block of the array $A_{CM}$, when provided, to provide a sum for all window positions on array $A_{CM}$ to form a completed spike count map 408.

The window 410 could be moved in different paths over the array $A_{CM}$ than that described here, such as raster order instead or any other order found to be efficient or advantageous. The ordering of the sums matches the relative window positions on the array $A_{CM}$ in the spike count map 408 but could be different when so desired.

By one form, the spike count map 408 may be used directly as the input spike data to the encoder. The downsampling example here, however, also binarizes the spike count map 408 to further reduce the computational load of the system without significant effect on the quality of the results.

Figure 7:
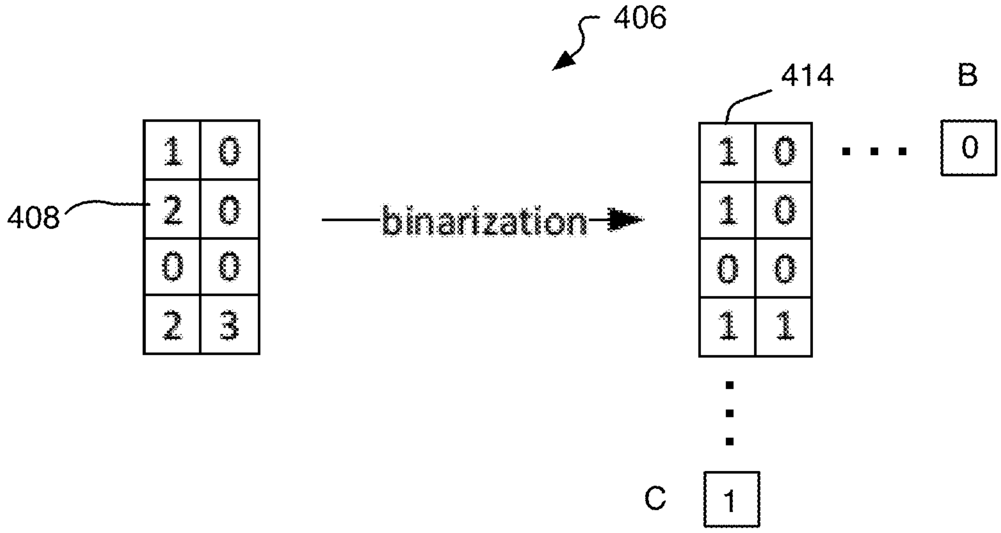

Referring to FIG. 7, a binarization stage 406 then may be performed where any non-zero sum in the spike count map 408 is changed to a 1, and all other spaces are maintained as 0. This forms a binary spike map 414, also referred to herein as a spike group map, that may be input to the encoder NN as an array. Each column on the spike group map 414 may have a spike group indicator that indicates which channels have at least one spike within a sample duration (or in other words, the window size or width) of a number of samples. The spike group map 414 may have C rows (or channels) and B columns each for a binary (or other) indicator of a different window position (or window width column). Thus, the encoder still may operate to provide magnitudes simply by using binary spike group indicators, rather than a spike count, that indicate at least one spike is present as long as the window duration is not too long. Whether or not using the spike group map 414 as direct input to the encoder NN, by one form, the window duration should be aligned with inverse short-time Fourier transform (iSTFT) parameters or other parameters of an inverse FFT to be performed during reconstruction of the signal after the encoding. Thus, the window size and hop size for downsampling should be equal to, or smaller than, the sampling parameters of the iSTFT settings.

Figures 8A, 8B:
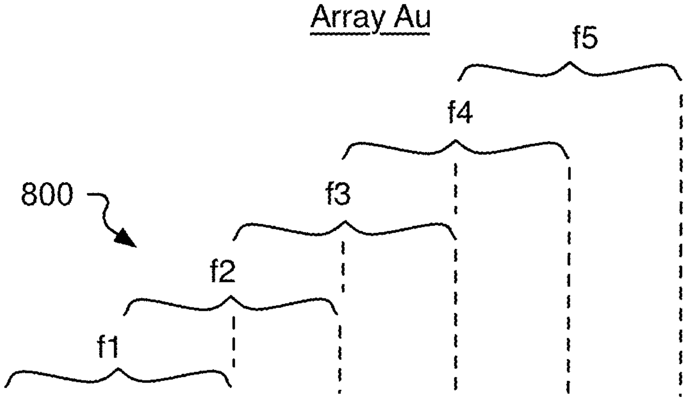
FIG. 8A is a schematic diagram of an ungrouped array of spike data according to at least one of the implementations herein.
FIG. 8B is a schematic diagram of a grouped array of spike data according to at least one of the implementations herein.

Referring to FIGS. 8A-8B, and whether or not downsampling has already been performed, process 300 may include "group the spikes to form NN input" 306. Spike grouping or accumulation may be performed to reduce input tensor size by reducing the number of samples (or number of spike group indictors from the previous downsampling) to a single value for an individual frame. The spike grouping can also increase the quality or accuracy of the system by forming a continuous representation of the spikes over time by overlapping the frames to increase the number of frames to be processed, rather than using distinct consecutive time frames. Thus, this spike grouping operation 306 may include "form overlapping frames" 308. Various techniques can be used to accomplish this including spike grouping that is time-binned, data-driven time binned, or event-binned. Otherwise, an exponential feature approach may be used. The example herein uses time-binned spike grouping, and whether or not downsampling was performed before the spike grouping. The spike grouping operation may be performed by using example equation (2) and variable-defining equations (3) to (5):

$$A_g[c, j] = A_u \sum_{i=1}^{i=f_{size}} [c, i + j \cdot f_{shift}] \tag{2}$$

$$f_c = \left[ \frac{s_c}{f_{shift}} - 1 \right] \tag{3}$$

$$f_{size} = \frac{f_s \cdot f_t}{1000} \tag{4}$$

$$f_{shift} = \frac{f_s \cdot f_{shift\_t}}{1000} \tag{5}$$

where in equation (2), a grouped array $A_g$ is an array with grouped spikes, c is a channel count in an ungrouped array $A_u$ where each channel has a single row in the array $A_u$, and j is a frame count where each frame has one or more columns of the array $A_u$.

The ungrouped array $A_u$ may hold different types of temporal spike data depending on whether or not the spike data has already been downsampled. Thus, when no downsampling has occurred yet as described above, ungrouped array $A_u$ is, or may be similar to, the initial array $A_{CM}$ output from the cochlea model. In this case, each column of the ungrouped array is a different sample or sample time s where each sample s has a spike indicator of 0 or 1 to indicate a single spike is present at that channel and at that sample (or sample time) s. Thus, in this case, each single frame f at a frame location j on array $A_u$ has multiple samples s where each sample is in its own column on array $A_u$.

On the other hand, if the spike data was downsampled, then the definition of a sample s (or column) is different for the ungrouped array $A_u$ for equations (2) to (5) above. In this case, each column of the array $A_u$ has a spike group indicator that represents a sample s in array $A_u$ for purposes of the equations (2) to (5) above and ungrouped array $A_u$ is, or may be similar to, the spike group map 414 (FIG. 7). Each spike group indicator indicates whether or not at least one time sample of a series of consecutive time samples from the initial array $A_{CM}$ has a spike as described above with the spike group map 414. In this case, each frame fat a frame location j represents a group of spike group indicators across multiple columns of ungrouped array $A_u$. Thus, in this case, each column and each sample may refer to a single spike group indicator value from the downsampling for equations (2) to (5).

In either case (whether or not downsampling was performed), the total number of columns of the $A_u$ will be referred to as a total sample count (or sample time count) $s_c$ across an entire row of the array $A_u$. An ungrouped array $A_u$ 800 (FIG. 8A) shows channel rows C1 to C and sample columns S1 to $S_c$. each sample value (0 or 1) at each channel is either a single spike indicator or a spike group indicator of a group of downsampled samples as described above. Also in equation (2), i is the sample count within a single frame f, and a frame shift $f_{shift}$ is computed by equation (4) below. The dot between j and $f_{shift}$ is multiplication.

Equation (3) generates a total number of frames $f_c$ across an entire row of array $A_u$ based on the total sample count $s_c$ and while providing a frame shift $f_{shift}$ to generate overlapping frames. The frame shift $f_{shift}$ may be expressed in number samples (or number of columns on array $A_u$), or in other words, the number of samples (or number of columns) that overlap with at least one other frame though it could be more than one. The brackets indicate a cell computation. Thus, the total number of frames $f_c$ also is the number of frames, and in turn columns, generated for the array $A_g$ when overlapping the frames.

Equation (4) generates a frame size $f_{size}$ expressed in number of samples (or columns) in the frame. Also, a sampling rate $f_s$ is the sampling rate used to form the ungrouped array $A_u$, and is in samples/second or Hertz. A frame time $f_t$ is provided in milliseconds (ms) for example. Equation (5) generates the frame shift $f_{shift}$ which is in a number of samples (or columns) of ungrouped array $A_u$ while $f_{shift\_t}$ is the frame shift in time (such as milliseconds (ms)). By one example, a frame time of 2 ms was used with a frame shift of 1 ms (for an overlap of 50%). Such an overlap of frames is shown on array $A_u$ where frames f1 to f5 each have four samples (or columns) and overlap two samples (or columns) of the prior frame.

With this arrangement, multiple samples (or multiple spike group indicators from downsampling) in each frame are summed separately for each channel to form a single spike count (or spike group indicator count) for each frame and at each channel. This results in each column of the grouped array $A_g$ 850 (FIG. 8B) representing an entire frame f1-f5 for five columns in the illustrated example. By another example, assume a total number of channels C=5, while $f_{shift}$=3 samples, $f_{size}$=6 samples, and $S_c$=24 total samples in a row. In this case, grouped array $A_g$ will have 5 channels by 7 overlapping frame columns. It will be appreciated that the assignment of the rows and columns to channels and sample times of any of the arrays described herein may be transposed when so desired.

Thereafter, the grouped array $A_g$ may be provided for direct input to the encoder NN, and by either inputting the entire array or by inputting one column at a time, and in turn one frame representation at a time, into the encoder NN. The frames may be collected into an input internal NN buffer to hold multiple frames as needed so that relationships between frames can be analyzed by the neural network as described below.

Process 300 may include "encode the spike data into spectrogram data" 310. This refers to a spike (or cochleogram data or domain)-to-magnitude (or spectrogram data or domain) conversion. This operation 310 may include "generate a spectrum of audio signal magnitudes of multiple channels at individual frames of a sequence of frames" 312.

Figure 9A:
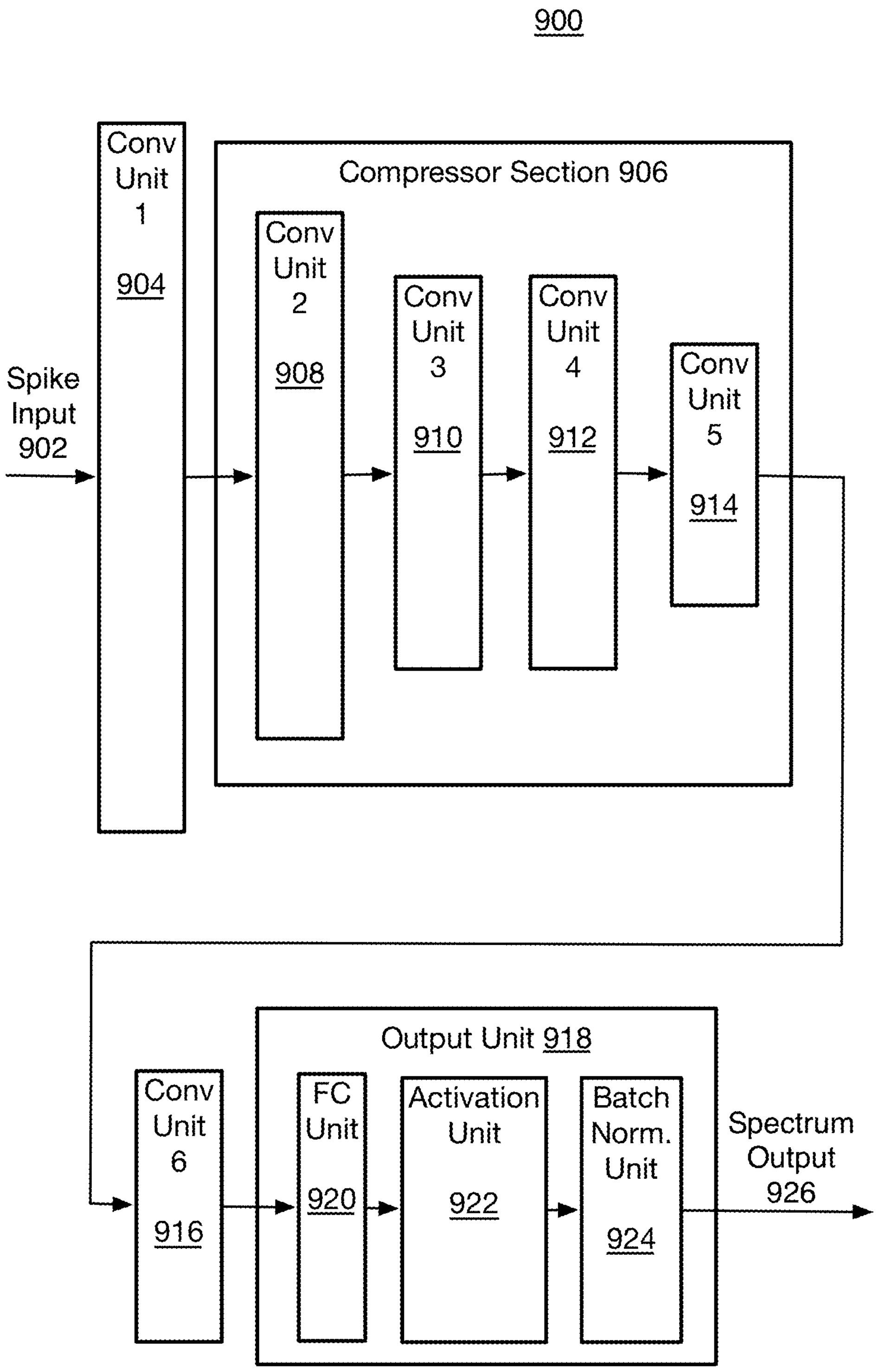
FIG. 9A is a schematic diagram of encoder neural network architecture according to at least one of the implementations herein.
Figure 9B:
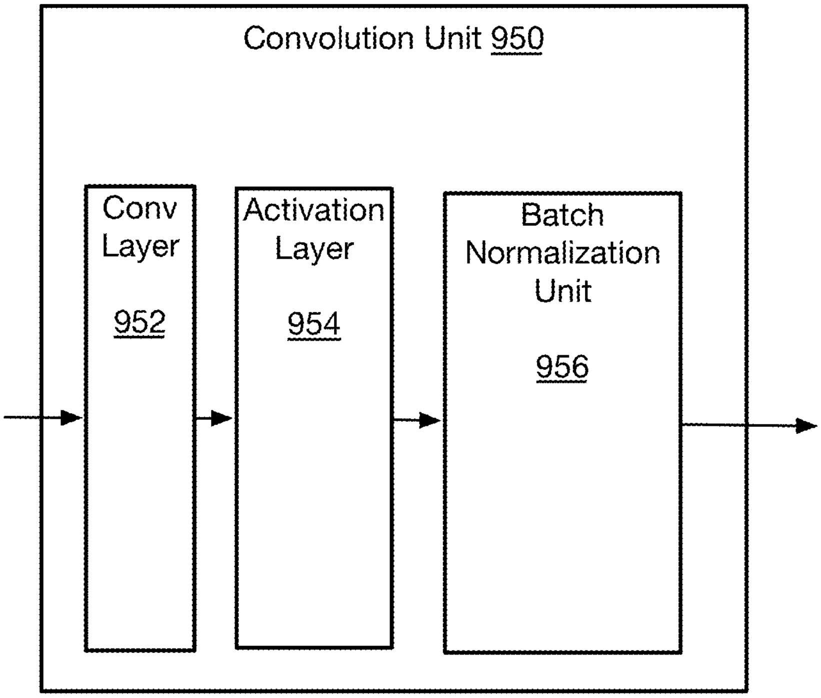
FIG. 9B is a schematic diagram of a component of the encoder neural network architecture of FIG. 8 and according to at least one of the implementations herein.

Referring to FIGS. 9A-9B for more detail, the generating 312 of the magnitude spectrum may include "use a neural network to perform the conversion" 314. Here a neural network may be trained to convert or encode the spikes into spectrogram data including magnitudes (or amplitudes) of frequency components to form spectrums that can be sufficient to form a spectrogram if so desired. In fact, the neural network is able to increase reconstructed audio signal quality despite the highly compressed input spike data from the grouped array $A_g$ for example.

An encoder NN 900 (FIG. 9A) has an example architecture or topology that has been found to generate magnitude spectrums that result in the high quality reconstructed audio signals. The encoder NN 900 encodes (or maps) grouped spikes to spectrum magnitude representation by finding dependencies between spiking channels and frames. These dependencies are believed to indicate spike density patterns, such as on a cochleogram that maps spikes per channel over time, that are similar to magnitude patterns on a spectrogram that maps magnitudes per frequency over time. Also, the neural network may be arranged to change a resolution of the input data to fit targets' dimensions, such as a set frequency and sampling time resolutions of inverse FFT units that can reconstruct an audio signal.

The encoder NN 900 has multiple convolutional units. Some of the convolutional units analyze the channel interrelationships regardless of time, and some of the convolutional units analyze the relationships between the channels and time. For example, encoder NN 900 has convolutional units numbered 1 (904) to 6 (916). The first convolutional unit 1 (904) receives a surface or plane that is a number of channels by number of sample-time based frames forming the grouped array $A_g$ or other array as described above (herein channel refers to a frequency bin rather than a separate NN input surface channel).

The convolutional units 1 (904), 4 (912), and 6 (916) analyze relationships between channels without factoring time dependences. These units have a pointwise kernel of 1×1 and a stride of 1 so that the resolution of the input surface or array does not change for either the time resolution or channel resolution of the propagating data.

Another group of the convolutional units 2 (908), 3 (910), and 5 (914) analyze the relationships between channels and time, and change the time resolution of the propagating data, and here to reduce the time resolution. These convolutional units 2 (908), 3 (910), and 5 (914) may be considered to form a compression section 906 of the encoder NN 900, and each have a 1×4 kernel where the kernel extends across multiple frames for a single channel, and a stride of 2 to perform the convolution. Table 1 below shows one possible arrangement of the convolutional units to show how each convolutional unit affects time resolution or data.

TABLE 1

Time frames count reduction by each convolutional unit in spike to spectrum magnitude encoder for wave signal (4 second length)

| Conv Unit Number (FIG. label no.) | Block Input Times Frames Count | Block Output Times Frames Count |
|---|---|---|
| 1 (904) | 4000 | 4000 |
| 2 (908) | 4000 | 2000 |
| 3 (910) | 2000 | 1000 |
| 4 (912) | 1000 | 1000 |
| 5 (914) | 1000 | 500 |
| 6 (916) | 500 | 500 |

Each convolutional unit 1 (904) to 6 (916) may have an arrangement the same as convolution unit (or module) 950 (FIG. 9B). This may include, in order, a one dimensional (1-D) convolutional layer 952 where 1-D refers to the single dimension pointwise 1×1 kernels or single channel 1×4 kernels, an activation layer 954, and a batch normalization layer 956, although other types of layers could support the convolutional layer 852 as well. In the current example, the convolution is as described above, the activation layer 954 may perform rectified linear unit (ReLU), parametric ReLU (PReLU), or other adequate activation functions, and the normalization layer may implement known NN normalization algorithms. These units are arranged to maintain the initial number of channels (256 in the present example) throughout the encoder NN without reducing the number of channels.

Once through the six convolutional units 904 to 916 of the encoder NN 900, the data is propagated through an output unit 918 that has a fully connected (FC) layer 920, an activation layer 922 that may use activation functions as mentioned with the convolutional units 904 to 916, and a batch normalization layer 924 that operates known normalization functions. The output is either an array or vector by vector of frames with a magnitude spectrum for each frame. The magnitude spectrums may or may not be used to form a spectrogram as desired.

The training of the encoder NN is performed by using supervised training. With tests that were performed for the disclosed method and system, a mean-square-error (MSE) loss function is calculated for the training and with usage of reconstructed audio signal waveform files and reference clean files (or targets). A training dataset had 2000 examples and 200 signals in an evaluation set. An optimizer "RAdam" was used in one form, and with a learning rate equal to 0.002, a weight decay=1e-5, batch size=8, and a topology for 100 epochs. The dataset was Speecon En-Us with clean speech only. A four second signal was used for the training. If the signal was longer, it was trimmed. If a signal was too short, zero-padding was added on the end of the signal.

While the magnitude spectrograms could be used directly for pre-processing and/or end applications, here process 300 may include "convert the spectrogram data into a reconstructed audio signal with a single varying amplitude in a time domain" 316. Here, the output spectrum from the encoder NN is input to an inverse FFT or similar mechanism to generate a single signal combining the frequencies to form a time domain audio signal with a single varying amplitude as the magnitude of the signal.

This operation 316 may include "re-use the phase from the original audio signal" 318. Since phase of a particular frequency is not carried over well with in the cochleogram or spike data, it is difficult to reconstruct full audio signals directly from the spikes. Instead, the magnitudes of the output spectrum may be combined to spectrum phases obtained from the original signal prior to spike-decoding into the cochleogram spike data. For example, the angular spectrum (or phase) of a particular frequency (or channel) may be read (or detected by impulse transmissions), and the timing of the signals for those frequencies may be adjusted to provide the correct phase before being combined at the inverse FFT.

Process 300 may include "use the reconstructed audio signal to perform further audio processing" 320. As mentioned above, the reconstructed audio signal may be used for pre-processing operations such as DNS or other noise removal audio signal refinement and/or modification. Whether or not pre-processed, the reconstructed audio signal then may be used by end applications such as ASR, WoV, KPD, speaker recognition (SR), audio source detection (angle of arrival (AOA) detection), as well as many others.

Also, the disclosed method may be implemented in firmware and one or more dedicated audio chips. A number of the NN operations herein may be offloaded to a Gaussian and neural accelerator (GNA), for example. Also, idle graphics processing units (GPUs) can be used to take up at least some of the computational load to process the audio neural network as well.

Experimental Results

The disclosed system and method were tested by training the Zilany cochlea model mentioned above to generate spikes from an input audio signal, and then to input those spikes to a cochleogram to spectrogram data encoder described above. The cochlea model is arranged to provide 16 channels each with 16 fibers for 256 spiking channels in total. The spike data output from the cochlea model was provided at 100 kHz and downsampled to 1 kHz. Spike grouping was performed by using 2 ms frames with 1 ms overlaps. As a target for training the encoder neural network, the network was tested on 200 utterances and was arranged to output a magnitude spectrum of 256 channels. The magnitudes were calculated by using a fast Fourier transform (FFT) and with 32 ms frames with an 8 ms hop.

Figure 10:
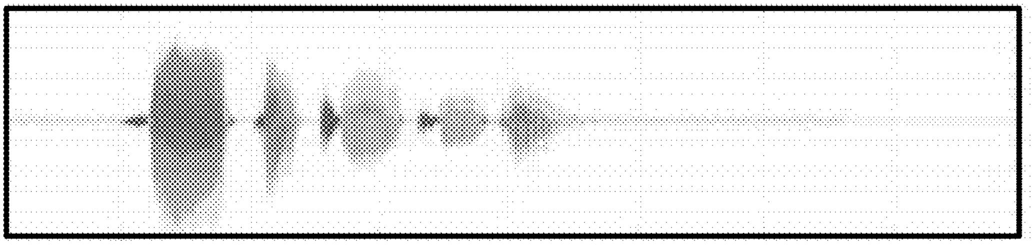
FIG. 10 is a graph showing an input time domain waveform audio signal.
Figure 11:
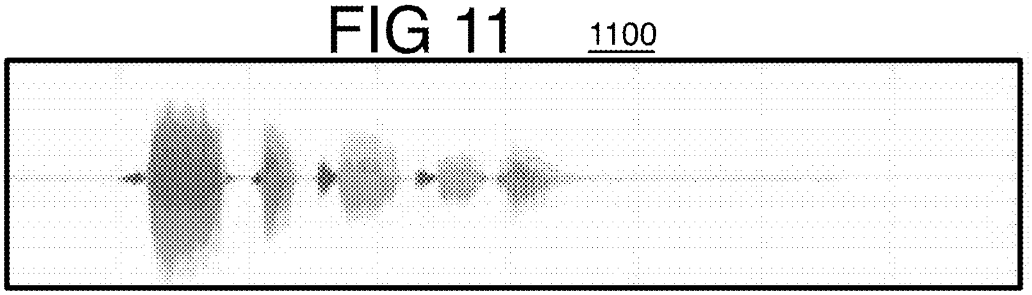
FIG. 11 is a graph showing a reconstructed time domain waveform audio signal generated by using an encoder according to at least one of the implementations herein.
Figure 12:
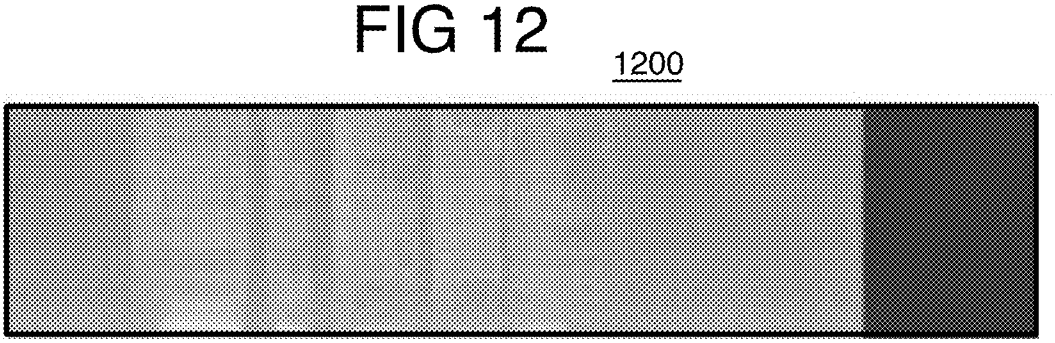
FIG. 12 is a graph showing a spectrogram of the input time domain waveform audio signal.
Figure 13:
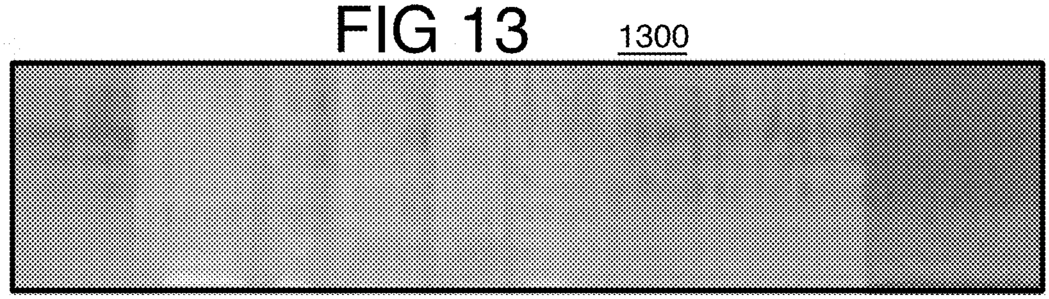
FIG. 13 is a graph showing a spectrogram of the reconstructed time domain waveform audio signal generated by using the encoder according to at least one of the implementations herein.

An audio signal graph 1000 (FIG. 10) shows the original audio signal waveform. An audio signal graph 1100 (FIG. 11) shows the reconstructed audio signal waveform output from the spike-to-spectrogram encoder. The original audio signal had magnitudes graphed on a spectrogram 1200 (FIG. 12). The encoder output audio signal magnitudes were graphed on a spectrogram 1300 (FIG. 13). The mean square error (MSE) of the test was 0.0978.

Data also was gathered to determine the compression ratio of the system and method described herein with the cochleogram-to-spectrogram data encoder. It should be noted, however, that since the spikes represent events, i.e., each spike is an event, the system effectively only performs calculations when an event occurs and a spike is received from the cochleogram data input to the encoder. Thus, to compare the input cochleogram data to an output spectrogram representation from the encoder, the analysis parameters must be considered since an amount of data being processed in both representations indicate the compression ratio and will depend on their analysis parameters. Specifically for the spectrogram, the amount of data being processed will depend on FFT resolution (or number of frequency bins), analysis hop size, sample rate, and sample resolution. The amount of data being processed at the input (or cochleogram data) will depend on a number of frequency channels being used, down-sampling factor, and sample rate. Spectrograms in speech analysis are typically calculated for an audio signal that is sampled with a 16 kHz sample rate, while a cochleogram sample rate of 100 kHz is used. Table 2 below shows the compression rate for various spectrogram data configurations, including FFT size, hop size, and sample resolution, analyzed at the encoder NN, and Table 3 shows the compression ratios depending on variations of the cochleogram data, including number of channels, downsampling factor, and sparsity, input to the encoder. The resulting compression ratios achieved by using the downsampled and grouped cochleogram-based spike data input to the encoder varies from 2.3 to 36.4, depending on the configuration. This shows the disclosed system and method can obtain beneficial reductions in the amount of data for higher performance.

TABLE 2

Amount of data for various spectrogram configurations and compression vs cochleogram

| Config | FFT size | Hop size | Sample resolution [bits] | Amount of data [kb/s] | Cochleogram compression ratio |
|---|---|---|---|---|---|
| 1 | 256 | 64 | 32 | 1000 | 36.4 |
| 2 | 256 | 64 | 16 | 500 | 18.2 |
| 3 | 256 | 64 | 8 | 250 | 9.1 |
| 5 | 256 | 128 | 16 | 250 | 9.1 |
| 6 | 512 | 128 | 16 | 500 | 9.1 |
| 7 | 512 | 256 | 16 | 250 | 4.6 |
| 8 | 1024 | 256 | 16 | 500 | 4.6 |
| 9 | 1024 | 512 | 16 | 250 | 2.3 |

TABLE 3

Amount of data for various cochleogram configurations

| Configuration | Channel counts | Down-sample factor | Sparsity [%] | Amount of data [kb/s] |
|---|---|---|---|---|
| 1 | 128 | 1 | 0.37 | 46.3 |
| 2 | 128 | 10 | 3.12 | 39.0 |
| 3 | 128 | 100 | 21.95 | 27.4 |
| 4 | 256 | 1 | 0.37 | 92.5 |
| 5 | 256 | 10 | 3.12 | 78.0 |
| 6 | 256 | 100 | 21.95 | 54.9 |
| 7 | 512 | 1 | 0.37 | 185.0 |
| 8 | 512 | 10 | 3.12 | 156.0 |
| 9 | 512 | 100 | 21.95 | 109.8 |

Also, the effect of the downsampling was tested as well, and it was found there is no significant drop in quality with greater downsampling. A Table 4 shown below compares average values of means square error (MSE) metric (equation 5), signal-to-distortion (SDR) metric (equation 6) and scale-invariant signal-to-noise ratio (SI-SNR) metric (equation 7) calculated for two encoders trained separately with down-sampling factor 1 or 100. Metrics were calculated for a test set that consists of 200 utterances. The same dataset mentioned above for testing is used here. The error measurement equations are as follows.

$$MSE = \frac{1}{n}\sum_{t=1}^{n}(x_t - \hat{x}_t)^2 \tag{6}$$

$$SDR = 10 \cdot \log_{10}\frac{\|x\|^2}{\|x - \hat{x}\|^2} \tag{7}$$

$$SI - SNR = 10 \cdot \log_{10}\frac{\|\alpha \cdot x\|^2}{\|\alpha \cdot x - \hat{x}\|^2} \tag{8}$$

$$\alpha = \frac{x^T \cdot \hat{x}}{\|x\|^2} \tag{9}$$

where ratio $\alpha$ in equation (9) is used in equation (8), x is a target audio signal, and $\hat{x}$ is the signal reconstructed from spikes using the disclosed method.

The difference in quality of encoder with down-sampled (down-sampling factor 100) and original spikes (down-sampling factor 1) is smaller than 2 dB of SI-SNR. Thus, based on the MSE (where a difference between the two encoders was smaller than 0.01), the down-sampling does not impact reconstruction quality significantly. Finally, even though SI-SNR provides an error close to 14 dB, which may be considered slightly too low for actual use, the present small training sample (a mere 200 utterances) was used to prove the conversion from cochleogram to spectrogram data could be achieved at all regardless of quality, and a much larger training dataset should be used (1 million samples) to improve the quality.

TABLE 4 metrics comparison for spike-to-magnitude spectrum encoder trained with different down-sampling factors:

| Config | Channels count | Down-sampling factor | MSE | SDR [dB] | SI-SNR [dB] |
|---|---|---|---|---|---|
| 1 | 256 | 1 | 0.0978 | 14.52 | 15.74 |
| 2 | 256 | 100 | 0.1063 | 13.72 | 13.92 |

In addition, any one or more of the operations of the process in FIG. 3, may be undertaken in response to instructions provided by one or more computer program products. Such program products may include signal bearing media providing instructions that, when executed by, for example, a processor, may provide the functionality described herein. The computer program products may be provided in any form of one or more machine-readable media. Thus, for example, a processor including one or more processor core(s) may undertake one or more of the operations of the example processes herein in response to program code and/or instructions or instruction sets conveyed to the processor by one or more computer or machine-readable media. In general, a machine-readable medium may convey software in the form of program code and/or instructions or instruction sets that may cause any of the devices and/or systems to perform as described herein. The machine or computer readable media may be a non-transitory article or medium, such as a non-transitory computer readable medium, and may be used with any of the examples mentioned above or other examples except that it does not include a transitory signal per se. It does include those elements other than a signal per se that may hold data temporarily in a "transitory" fashion such as RAM and so forth.

As used in any implementation described herein, the term "module" refers to any combination of software logic, firmware logic, hardware logic, and/or circuitry configured to provide the functionality described herein. The software may be embodied as a software package, code and/or instruction set or instructions, and "hardware", as used in any implementation described herein, may include, for example, singly or in any combination, hardwired circuitry, programmable circuitry, state machine circuitry, fixed function circuitry, execution unit circuitry, and/or firmware that stores instructions executed by programmable circuitry. The modules may, collectively or individually, be embodied as circuitry that forms part of a larger system, for example, an integrated circuit (IC), system on-chip (SoC), and so forth.

As used in any implementation described herein, the term "logic unit" refers to any combination of firmware logic and/or hardware logic configured to provide the functionality described herein. The "hardware", as used in any implementation described herein, may include, for example, singly or in any combination, hardwired circuitry, programmable circuitry, state machine circuitry, and/or firmware that stores instructions executed by programmable circuitry. The logic units may, collectively or individually, be embodied as circuitry that forms part of a larger system, for example, an integrated circuit (IC), system on-chip (SoC), and so forth. For example, a logic unit may be embodied in logic circuitry for the implementation firmware or hardware of the coding systems discussed herein. One of ordinary skill in the art will appreciate that operations performed by hardware and/or firmware may alternatively be implemented via software, which may be embodied as a software package, code and/or instruction set or instructions, and also appreciate that logic unit may also utilize a portion of software to implement its functionality.

As used in any implementation described herein, the term "component" may refer to a module or to a logic unit, as these terms are described above. Accordingly, the term "component" may refer to any combination of software logic, firmware logic, and/or hardware logic configured to provide the functionality described herein. For example, one of ordinary skill in the art will appreciate that operations performed by hardware and/or firmware may alternatively be implemented via a software module, which may be embodied as a software package, code and/or instruction set, and also appreciate that a logic unit may also utilize a portion of software to implement its functionality.

The terms "circuit" or "circuitry," as used in any implementation herein, may comprise or form, for example, singly or in any combination, hardwired circuitry, programmable circuitry such as computer processors comprising one or more individual instruction processing cores, state machine circuitry, and/or firmware that stores instructions executed by programmable circuitry. The circuitry may include a processor ("processor circuitry") and/or controller configured to execute one or more instructions to perform one or more operations described herein. The instructions may be embodied as, for example, an application, software, firmware, etc. configured to cause the circuitry to perform any of the aforementioned operations. Software may be embodied as a software package, code, instructions, instruction sets and/or data recorded on a computer-readable storage device. Software may be embodied or implemented to include any number of processes, and processes, in turn, may be embodied or implemented to include any number of threads, etc., in a hierarchical fashion. Firmware may be embodied as code, instructions or instruction sets and/or data that are hard-coded (e.g., nonvolatile) in memory devices. The circuitry may, collectively or individually, be embodied as circuitry that forms part of a larger system, for example, an integrated circuit (IC), an application-specific integrated circuit (ASIC), a system-on-a-chip (SoC), desktop computers, laptop computers, tablet computers, servers, smartphones, etc. Other implementations may be implemented as software executed by a programmable control device. In such cases, the terms "circuit" or "circuitry" are intended to include a combination of software and hardware such as a programmable control device or a processor capable of executing the software. As described herein, various implementations may be implemented using hardware elements, software elements, or any combination thereof that form the circuits, circuitry, processor circuitry. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Figure 14:
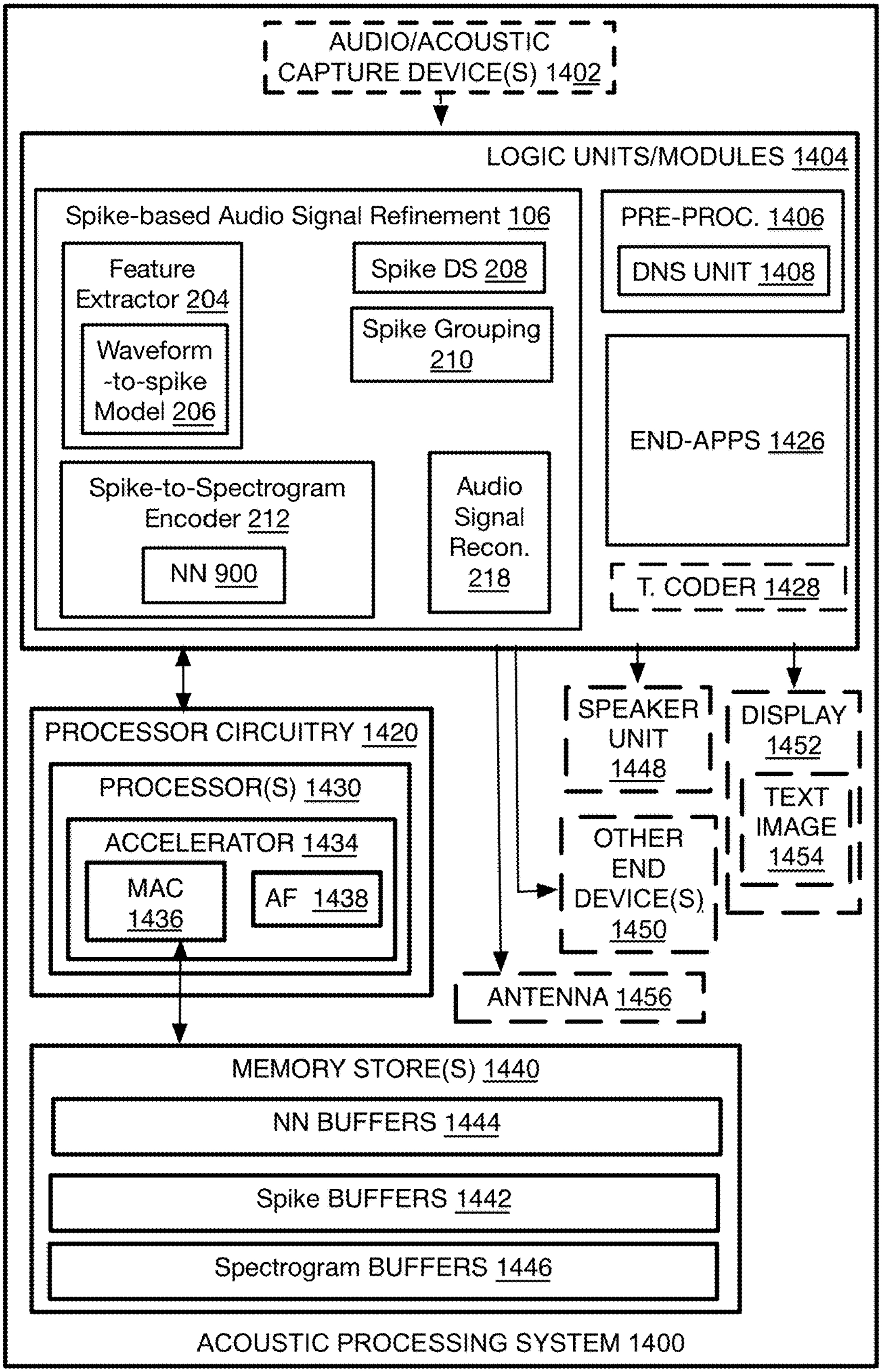
FIG. 14 is a schematic diagram of an example system.

Referring to FIG. 14, an example audio processing system or device 1400, may be audio processing system 100, and is arranged in accordance with at least some implementations of the present disclosure. In various implementations, the example audio processing system 1400 may have one or more audio capture devices 1402 to form or receive audio signal data. This can be implemented in various ways. Thus, in one form, the audio processing system 1400 is a device, or is on a device, with one or more microphones, and one or a network of the devices 1402 provides the audio signals or data used for spike-based audio processing, and other audio processing, described above and that may be performed by one of the networked devices 1402. In other examples, the audio processing system 1400 may be in communication with one or a network of microphones, and may be remote from these audio signal capture devices 1402 such that logic modules (or circuits or units) 1404 may communicate remotely with, or otherwise may be communicatively coupled to, the microphones for further processing of the audio signals or data.

In either case, such technology may include a telephone, a smart phone, a tablet, laptop or other computer, dictation machine, other sound recording machine, a mobile device or an on-board device, or any combination of these. Thus, in one form, audio capture device 1402 may include audio capture hardware including one or more sensors as well as actuator controls. These controls may be part of a sensor module or component for operating the sensor. The sensor component may be part of the audio capture device 1402, or may be part of the logical modules 1404 or both. Such sensor component can be used to convert sound waves into an electrical audio signal. The audio capture device 1402 also may have an A/D converter, other filters, and so forth to provide a digital signal for audio signal processing.

In the illustrated example, the logic units, modules, or circuitry 1404 may have the spike-based audio signal refinement unit (or generator) 106 (or 200) and as described above with FIGS. 1-2. The circuitry 1404 also may include a pre-processing unit 1406 to handle pre-processing tasks that may be needed at least for the end audio processing application to be used. By one form, the pre-processing unit 1406 may include a dynamic noise suppression (DNS) unit 1408 as well as others described above.

The logic modules 1404 also may include a transmission coder 1428 to transmission encode the output audio for transmission to another device when needed. These units may be used to perform the operations described above where relevant and as suggested by the similarity of the title of the unit to those units described above.

The audio processing system 1400 may have processor circuitry 1420 that forms one or more processors 1430, such as the Intel Atom®, and may include digital signal processors (DSPs) and/or one or more dedicated audio accelerators 1434 that may include firmware and one or more dedicated audio chips. For example, neural network operations of the encoder 214 or other audio processing, such as for the DNS, may be offloaded to a Gaussian and neural accelerator (GNA) that has multiply-accumulate circuits (MACs) 1436, activation function circuits 1438, as well as other circuits, for example.

The system 1400 also may have memory stores 1440 that may have neural network internal buffers such as spike buffers 1442, NN(operation, intermediate data, or layer) buffers 1444 including bias and weight buffers for example, and spectrogram buffers 1446. These buffers may hold any neural network related data including inputs, outputs, intermediate features, the parameters, and so forth.

The system also optionally may have at least one local or remote communicatively connected speaker unit 1448 to emit audio based on the input audio signals, one or more displays 1452 to provide images 1454 of text, for example, as a visual response to the audio signals, other end device(s)

1450 to perform actions in response to the audio signal, and antenna 1456 to transmit or receive data as needed.

In one example implementation, the audio processing system 1400 may have the speaker unit 1448, processor circuitry 1420 forming at least one processor 1430 communicatively coupled to the speaker 1448, and memory 1440 communicatively coupled to the processor 1430. The antenna 1456 may be provided to transmit the output signals or other relevant commands to other devices that may use the output signals. Otherwise, the results of the output signals may be stored in memory 1440. As illustrated, any of these components may be capable of communication with one another and/or communication with portions of logic modules 1404 and/or audio capture device 1402. Thus, processors 1430 may be communicatively coupled to the audio capture device 1402, the logic modules 1404, and the memory 1440 for operating those components.

Although audio processing system 1400, as shown in FIG. 14, may include one particular set of blocks or actions associated with particular components or modules, these blocks or actions may be associated with different components or modules than the particular component or module illustrated here.

Figure 15:
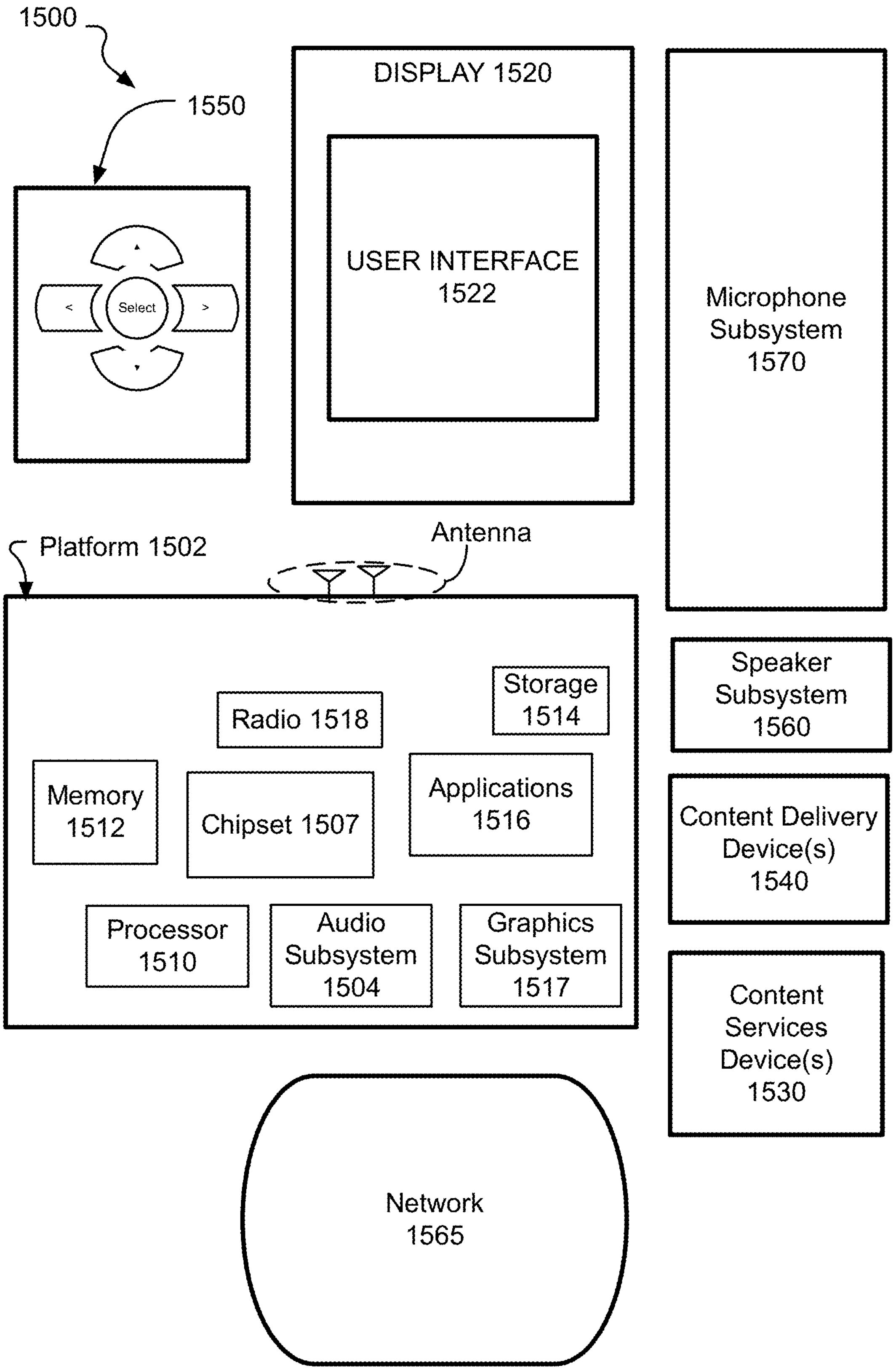
FIG. 15 is a schematic diagram of another example system.

Referring to FIG. 15, an example system 1500 in accordance with the present disclosure operates one or more aspects of the acoustic processing system described herein. It will be understood from the nature of the system components described below that such components may be associated with, or used to operate, certain part or parts of the audio or speech processing system described above. In various implementations, system 1500 may be a media system although system 1500 is not limited to this context. For example, system 1500 may be incorporated into, or receive acoustic signals or data from, one or multiple microphones, or multiple systems 1500 networked together may be used when each one contributes a different microphone, personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth, but otherwise any acoustic processing device receiving acoustic signals or audio signal data of one or more (or a network of) microphones.

In various implementations, system 1500 includes a platform 1502 coupled to a display 1520. Platform 1502 may receive content from a content device such as content services device(s) 1530 or content delivery device(s) 1540 or other similar content sources. A navigation controller 1550 including one or more navigation features may be used to interact with, for example, platform 1502, speaker subsystem 1560, microphone subsystem 1570 to provide the acoustic signals or data described above, and/or display 1520. Some of these components are described in greater detail below.

In various implementations, platform 1502 may include any combination of a chipset 1507, processor 1510, memory 1512, storage 1514, audio subsystem 1504, graphics subsystem 1517, applications 1516 and/or radio 1518. Chipset 1507 may provide intercommunication among processor 1510, memory 1512, storage 1514, audio subsystem 1504, graphics subsystem 1517, applications 1516 and/or radio 1518. For example, chipset 1507 may include a storage adapter (not depicted) capable of providing intercommunication with storage 1514.

Processor 1510 may be implemented as a Complex Instruction Set Computer (CISC) or Reduced Instruction Set Computer (RISC) processors; x86 instruction set compatible processors, multi-core, or any other microprocessor or central processing unit (CPU). In various implementations, processor 1510 may be dual-core processor(s), dual-core mobile processor(s), and so forth.

Memory 1512 may be implemented as a volatile memory device such as, but not limited to, a Random Access Memory (RAM), Dynamic Random Access Memory (DRAM), or Static RAM (SRAM).

Storage 1514 may be implemented as a non-volatile storage device such as, but not limited to, a magnetic disk drive, optical disk drive, tape drive, an internal storage device, an attached storage device, flash memory, battery backed-up SDRAM (synchronous DRAM), and/or a network accessible storage device. In various implementations, storage 1514 may include technology to increase the storage performance enhanced protection for valuable digital media when multiple hard drives are included, for example.

Audio subsystem 1504 may perform processing of audio such as acoustic signals to perform the noise suppression described herein and then to emit the audio or for other applications such as speech recognition and/or voice recognition. The audio processing techniques described herein may be implemented in various hardware architectures. Thus, the audio subsystem 1504 may comprise one or more processing units, memories, and shared or audio dedicated accelerators, such as a GNA. Such an audio subsystem may be integrated into processor 1510 or chipset 1507. Alternatively, a discrete audio processor may be used. Thus, in some implementations, the audio subsystem 1504 may be a stand-alone card communicatively coupled to chipset 1507. As still another implementation, the audio functions may be provided by a general purpose processor, including a multi-core processor. An interface may be used to communicatively couple the audio subsystem 1504 to a speaker subsystem 1560, microphone subsystem 1570, and/or display 1520. In further implementations, the functions may be implemented in a consumer electronics device.

Graphics subsystem 1517 may perform processing of images such as still or video for display. Graphics subsystem 1517 may be a graphics processing unit (GPU) or a visual processing unit (VPU), for example. An analog or digital interface may be used to communicatively couple graphics subsystem 1517 and display 1520. For example, the interface may be any of a High-Definition Multimedia Interface, Display Port, wireless HDMI, and/or wireless HD compliant techniques. Graphics subsystem 1517 may be integrated into processor 1510 or chipset 1507. In some implementations, graphics subsystem 1517 may be a stand-alone card communicatively coupled to chipset 1507.

Radio 1518 may include one or more radios capable of transmitting and receiving signals using various suitable wireless communications techniques. Such techniques may involve communications across one or more wireless networks. Example wireless networks include (but are not limited to) wireless local area networks (WLANs), wireless personal area networks (WPANs), wireless metropolitan area network (WMANs), cellular networks, and satellite networks. In communicating across such networks, radio 1518 may operate in accordance with one or more applicable standards in any version.

In various implementations, display 1520 may include any television type monitor or display. Display 1520 may include, for example, a computer display screen, touch screen display, video monitor, television-like device, and/or a television. Display 1520 may be digital and/or analog. In various implementations, display 1520 may be a holographic display. Also, display 1520 may be a transparent surface that may receive a visual projection. Such projections may convey various forms of information, images, and/or objects. For example, such projections may be a visual overlay for a mobile augmented reality (MAR) application. Under the control of one or more software applications 1516, platform 1502 may display user interface 1522 on display 1520.

In various implementations, content services device(s) 1530 may be hosted by any national, international and/or independent service and thus accessible to platform 1502 via the Internet, for example. Content services device(s) 1530 may be coupled to platform 1502 and/or to display 1520, speaker subsystem 1560, and microphone subsystem 1570. Platform 1502 and/or content services device(s) 1530 may be coupled to a network 1565 to communicate (e.g., send and/or receive) media information to and from network 1565. Content delivery device(s) 1540 also may be coupled to platform 1502, speaker subsystem 1560, microphone subsystem 1570, and/or to display 1520.

In various implementations, content services device(s) 1530 may include a cable television box, personal computer, network, telephone, Internet enabled devices or appliance capable of delivering digital information and/or content, and any other similar device capable of unidirectionally or bidirectionally communicating content between content providers and platform 1502 and speaker subsystem 1560, microphone subsystem 1570, and/or display 1520, via network 1565 or directly. It will be appreciated that the content may be communicated unidirectionally and/or bidirectionally to and from any one of the components in system 1500 and a content provider via network 1565. Examples of content may include any media information including, for example, video, music, medical and gaming information, and so forth.

Content services device(s) 1530 may receive content such as cable television programming including media information, digital information, and/or other content. Examples of content providers may include any cable or satellite television or radio or Internet content providers. The provided examples are not meant to limit implementations in accordance with the present disclosure in any way.

In various implementations, platform 1502 may receive control signals from navigation controller 1550 having one or more navigation features. The navigation features of controller 1550 may be used to interact with user interface 1522, for example. In embodiments, navigation controller 1550 may be a pointing device that may be a computer hardware component (specifically, a human interface device) that allows a user to input spatial (e.g., continuous and multi-dimensional) data into a computer. Many systems such as graphical user interfaces (GUI), and televisions and monitors allow the user to control and provide data to the computer or television using physical gestures. The audio subsystem 1504 also may be used to control the motion of articles or selection of commands on the interface 1522.

Movements of the navigation features of controller 1550 may be replicated on a display (e.g., display 1520) by movements of a pointer, cursor, focus ring, or other visual indicators displayed on the display or by audio commands. For example, under the control of software applications 1516, the navigation features located on navigation controller 1550 may be mapped to virtual navigation features displayed on user interface 1522, for example. In implementations, controller 1550 may not be a separate component but may be integrated into platform 1502, speaker subsystem 1560, microphone subsystem 1570, and/or display 1520. The present disclosure, however, is not limited to the elements or in the context shown or described herein.

In various implementations, drivers (not shown) may include technology to enable users to instantly turn on and off platform 1502 like a television with the touch of a button after initial boot-up, when enabled, for example, or by auditory command. Program logic may allow platform 1502 to stream content to media adaptors or other content services device(s) 1530 or content delivery device(s) 1540 even when the platform is turned "off." In addition, chipset 1505 may include hardware and/or software support for 8.1 surround sound audio and/or high definition (7.1) surround sound audio, for example. Drivers may include an auditory or graphics driver for integrated auditory or graphics platforms. In embodiments, the auditory or graphics driver may comprise a peripheral component interconnect (PCI) Express graphics card.

In various implementations, any one or more of the components shown in system 1500 may be integrated. For example, platform 1502 and content services device(s) 1530 may be integrated, or platform 1502 and content delivery device(s) 1540 may be integrated, or platform 1502, content services device(s) 1530, and content delivery device(s) 1540 may be integrated, for example. In various implementations, platform 1502, speaker subsystem 1560, microphone subsystem 1570, and/or display 1520 may be an integrated unit. Display 1520, speaker subsystem 1560, and/or microphone subsystem 1570 and content service device(s) 1530 may be integrated, or display 1520, speaker subsystem 1560, and/or microphone subsystem 1570 and content delivery device(s) 1540 may be integrated, for example. These examples are not meant to limit the present disclosure.

In various implementations, system 1500 may be implemented as a wireless system, a wired system, or a combination of both. When implemented as a wireless system, system 1500 may include components and interfaces suitable for communicating over a wireless shared media, such as one or more antennas, transmitters, receivers, transceivers, amplifiers, filters, control logic, and so forth. An example of wireless shared media may include portions of a wireless spectrum, such as the RF spectrum and so forth. When implemented as a wired system, system 1500 may include components and interfaces suitable for communicating over wired communications media, such as input/output (I/O) adapters, physical connectors to connect the I/O adapter with a corresponding wired communications medium, a network interface card (NIC), disc controller, video controller, audio controller, and the like. Examples of wired communications media may include a wire, cable, metal leads, printed circuit board (PCB), backplane, switch fabric, semiconductor material, twisted-pair wire, co-axial cable, fiber optics, and so forth.

Platform 1502 may establish one or more logical or physical channels to communicate information. The information may include media information and control information. Media information may refer to any data representing content meant for a user. Examples of content may include, for example, data from a voice conversation, videoconference, streaming video and audio, electronic mail ("email") message, voice mail message, alphanumeric symbols, graphics, image, video, audio, text and so forth. Data from a voice conversation may be, for example, speech information, silence periods, background noise, comfort noise, tones and so forth. Control information may refer to any data representing commands, instructions or control words meant for an automated system. For example, control information may be used to route media information through a system, or instruct a node to process the media information in a predetermined manner. The implementations, however, are not limited to the elements or in the context shown or described in FIG. 15.

Figure 16:
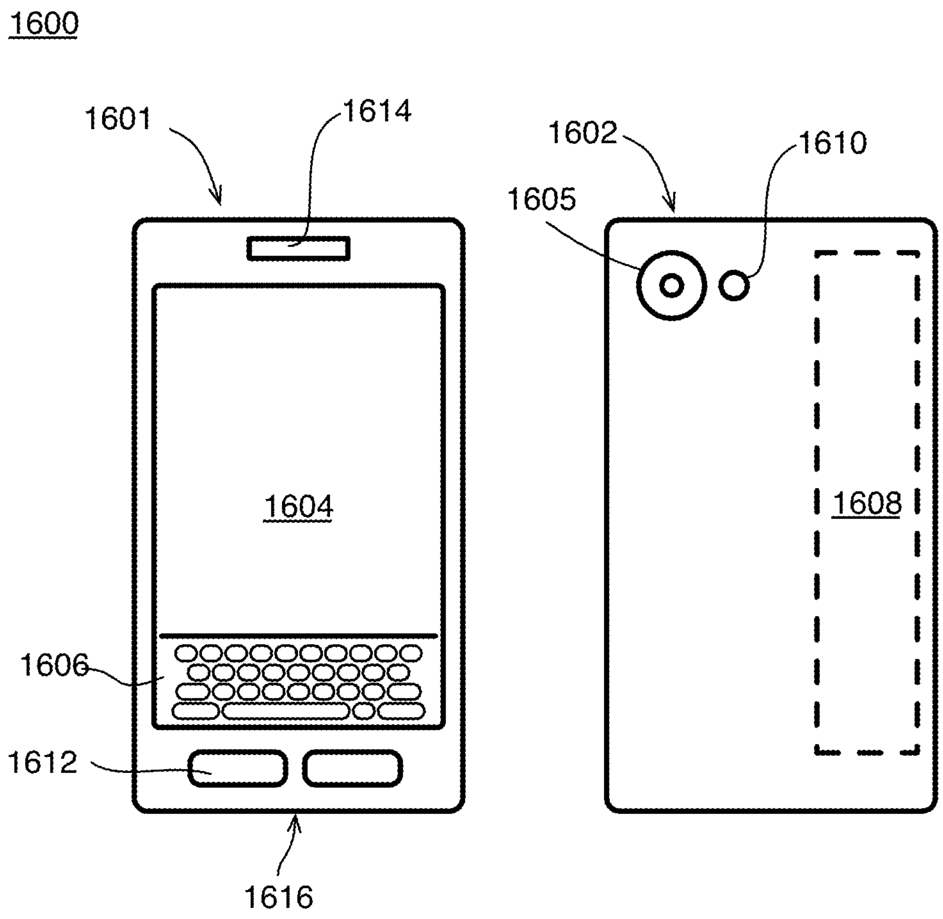
FIG. 16 is an example device, all arranged in accordance with at least some of the implementations of the present disclosure.

Referring to FIG. 16, a small form factor device 1600 is one example of the varying physical styles or form factors in which system 1400 or 1500 may be embodied. By this approach, device 1600 may be implemented as a mobile computing device having wireless capabilities. A mobile computing device may refer to any device having a processing system and a mobile power source or supply, such as one or more batteries, for example.

As described above, examples of a mobile computing device may include any device with an audio sub-system that receives acoustic signals or data from multiple microphones such as a personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet, or smart television), mobile internet device (MID), messaging device, data communication device, speaker system, microphone system or network, and so forth, and any other on-board (such as on a vehicle), or building, computer that may accept audio commands.

Examples of a mobile computing device also may include computers that are arranged to be worn by a person, such as a head-phone, head band, hearing aide, wrist computer, finger computer, ring computer, eyeglass computer, belt-clip computer, arm-band computer, shoe computers, clothing computers, and other wearable computers. In various embodiments, for example, a mobile computing device may be implemented as a smart phone capable of executing computer applications, as well as voice communications and/or data communications. Although some embodiments may be described with a mobile computing device implemented as a smart phone by way of example, it may be appreciated that other embodiments may be implemented using other wireless mobile computing devices as well. The implementations are not limited in this context.

As shown in FIG. 16, device 1600 may include a housing with a front 1601 and a back 1602, a display or screen 1604, an input/output (I/O) device 1606, and an antenna 1608. Device 1600 also may include navigation features 1612. Display 1604 may provide images processed by any suitable display unit for displaying information appropriate for a mobile computing device. I/O device 1606 may include any suitable I/O device for entering information into a mobile computing device. Examples for I/O device 1606 may include an alphanumeric keyboard, a numeric keypad, a touch pad, input keys, buttons, switches, rocker switches, software and so forth. Information also may be entered into device 1600 by way of a network of two or more microphones 1616. Such information may be processed by a separation and localization device as described herein as well as other acoustic mixing devices, speech and/or voice recognition devices, and so forth, as part of the device 1600. By one form, multiple devices 1600 spaced from each may be used to perform the acoustic data collection described above. Device 1600 also may provide audio responses via a speaker 1614 or visual responses via the screen 1604. The implementations are not limited in this context. The housing also may include a camera 1605 and an illuminator 1610.

Various forms of the devices and processes described herein may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an implementation is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one implementation may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor.

While certain features set forth herein have been described with reference to various implementations, this description is not intended to be construed in a limiting sense. Hence, various modifications of the implementations described herein, as well as other implementations, which are apparent to persons skilled in the art to which the present disclosure pertains are deemed to lie within the spirit and scope of the present disclosure.

The following examples pertain to further implementations.

In an example 1, a computer-implemented method of audio processing comprises receiving audio signal spike data from a cochlea model; encoding the spike data into spectrogram data comprising generating at least one spectrum of audio signal magnitudes of multiple channels at individual frames of a sequence of the frames; and converting the spectrogram data into a reconstructed audio signal with a single varying amplitude in a time domain.

In an example 2, the subject matter of example 1 can optionally include wherein the encoding comprises inputting the spike data to a neural network that outputs the spectrogram data.

In an example 3, the subject matter of example 2 can optionally include downsampling the spike data before inputting the spike data into the neural network.

In an example 4, the subject matter of example 2 or 3 can optionally include arranging downsampled spike data into overlapping frames before inputting a version of the overlapped frames into the neural network.

In an example 5, the subject matter of example 3 or 4 can optionally include wherein the downsampling comprises generating a spike group map wherein each value is a spike group indicator on the spike map that indicates whether or not a group of consecutive time samples has at least one spike.

In an example 6, the subject matter of example 5 can optionally include inputting the spike group map into the neural network.

In an example 7, the subject matter of example 5 can optionally include applying spike grouping to the spike group map to generate a spike group count map wherein each value on the spike group count map is a count of spike group indicators from the spike group map over a plurality of locations forming a single frame; and inputting the spike group count map into the neural network.

In an example 8, the subject matter of example 7 can optionally include grouping spikes so that the frames overlap.

In an example 9, the subject matter of example 2 can optionally include forming a version of overlapping frames of the spike data before inputting the spike into the neural network.

In an example 10, a computer implemented system comprises memory; processor circuitry forming at least one processor communicatively coupled to the memory and being arranged to operate by: receiving audio signal spike data from a cochlea model; inputting a version of the spike data into a neural network to output spectrums of audio signal frequency component magnitudes, each spectrum being of a different sample time; and generating a reconstructed time domain audio signal using the spectrums.

In an example 11, the subject matter of example 10 can optionally include wherein the spike data to be input to the neural network has a version of overlapping frames.

In an example 12, the subject matter of example 10 or 11 can optionally include wherein the neural network has multiple convolutional units to decrease the resolution of time samples represented while maintaining a representation of a same number of frequency channels throughout the neural network.

In an example 13, the subject matter of any one of example 10 to 12 can optionally include wherein the neural network has a plurality of convolutional units each having a pointwise convolutional layer.

In an example 14, the subject matter of any one of example 10 to 13 can optionally include wherein the neural network has a plurality of one-dimensional convolutional units each having a convolutional layer arranged to use a one-dimensional kernel that combines a number of time-based values while maintaining an initial number of frequency channels.

In an example 15, the subject matter of any one of example 10 to 14 can optionally include wherein the neural network has a sequence of six convolutional units each with a convolutional layer, wherein the second, third, and fifth convolutional units reduce the sample time or time frame resolution of propagating data at the neural network.

In an example 16, the subject matter of any one of example 10 to 15 can optionally include wherein the generating comprises obtaining angular spectrum phase data from a version of the audio signal data used to form the spike data, and using the phase data to reconstruct the audio signal with the magnitude spectrums.

In an example 17, the subject matter of any one of example 10 to 16 can optionally include wherein the neural network is arranged to receive spike data comprising a sequence of time samples that each show when a spike occurs at a plurality of channels in individual time samples.

In an example 18, At least one non-transitory computer readable medium comprising instructions thereon that when executed, cause a computing device to operate by: receiving audio signal data comprising cochlear-simulating spike data of a plurality of channels provided at each sample of a time sequence of samples; downsampling the spike data comprising determining a spike group indicator that indicates at least one spike exists for a group of the samples and for individual channels; and inputting a version of a plurality of the spike group indicators into a spike-to-magnitude encoder to output an audio magnitude spectrum.

In an example 19, the subject matter of example 18 can optionally include wherein the downsampling comprises generating a spike group map of spike group indicators that has a time sample resolution reduced from the cochlear-simulating spike data provided by a cochlea model without reducing a number of frequency channels provided by the cochlea model.

In an example 20, the subject matter of example 19 can optionally include applying spike grouping to generate a count map of a version of overlapping frames of the spike group indicators, wherein each frame has a count of multiple values of the spike group map from a same channel; and inputting the count map into the encoder.

In an example 21, the subject matter of any one of example 18, 19, or 20 can optionally include wherein the downsampling comprises moving a summing window to multiple positions over multiple time samples of a single channel to form a spike group indicator each at a different individual window position.

In an example 22, At least one non-transitory computer readable medium comprising instructions thereon that when executed, cause a computing device to operate by: receiving audio signal data comprising cochlear-simulating spike data; generating a spike group indicator map wherein each location on the map has a spike group indicator that indicates whether or not consecutive time samples of the spike data has at least one spike; generating counts of the spike group indicators with spikes and within a group of consecutive locations on the spike group indicator map; and inputting the counts into a neural network to output audio magnitude spectrums.

In an example 23, the subject matter of example 22 can optionally include using the magnitude spectrums to form a time domain audio signal.

In an example 24, the subject matter of example 22 or 23 can optionally include wherein the instructions cause the computing device to operate by downsampling the spike data before spike grouping the downsampled spike data.

In an example 25, the subject matter of any one of example 22, 23, or 24 can optionally include wherein the instructions cause the computing device to operate by applying denoising, dynamic noise suppression, blind source separation, or any combination of these to the reconstructed audio signal before performing audio processing of at least one of: wake-on-voice, keyword spotting, automatic speech recognition, speaker recognition, and angle of arrival detection on the reconstructed audio signal.

In a further example, at least one machine readable medium may include a plurality of instructions that in response to being executed on a computing device, causes the computing device to perform a method according to any one of the above examples.

In a still further example, an apparatus may include means for performing the methods according to any one of the above examples.

The above examples may include specific combination of features. However, the above examples are not limited in this regard and, in various implementations, the above examples may include undertaking only a subset of such features, undertaking a different order of such features, undertaking a different combination of such features, and/or undertaking additional features than those features explicitly listed. For example, all features described with respect to any example methods herein may be implemented with respect to any example apparatus, example systems, and/or example articles, and vice versa.

The invention claimed is:

1. A computer-implemented method of audio processing, comprising:
receiving audio signal spike data from a cochlea model;
encoding the spike data into spectrogram data comprising generating at least one spectrum of audio signal magnitudes of multiple channels at individual frames of a sequence of the frames; and
converting the spectrogram data into a reconstructed audio signal with a single varying amplitude in a time domain.

2. The method of claim 1 wherein the encoding comprises inputting the spike data to a neural network that outputs the spectrogram data.

3. The method of claim 2 comprising downsampling the spike data before inputting the spike data into the neural network.

4. The method of claim 3 comprising arranging downsampled spike data into overlapping frames before inputting a version of the overlapped frames into the neural network.

5. The method of claim 3 wherein the downsampling comprises generating a spike group map wherein each value is a spike group indicator on the spike map that indicates whether or not a group of consecutive time samples has at least one spike.

6. The method of claim 5 comprising inputting the spike group map into the neural network.

7. The method of claim 5 comprising applying spike grouping to the spike group map to generate a spike group count map wherein each value on the spike group count map is a count of spike group indicators from the spike group map over a plurality of locations forming a single frame; and inputting the spike group count map into the neural network.

8. The method of claim 7 comprising grouping spikes so that the frames overlap.

9. The method of claim 2 comprising forming a version of overlapping frames of the spike data before inputting the spike into the neural network.

10. A computer implemented system, comprising:
memory;
processor circuitry forming at least one processor communicatively coupled to the memory and being arranged to operate by:
receiving audio signal spike data from a cochlea model;
inputting a version of the spike data into a neural network to output magnitude spectrums of audio signal frequency component magnitudes, each spectrum being of a different sample time; and
generating a reconstructed time domain audio signal using the spectrums.

11. The system of claim 10 wherein the spike data to be input to the neural network has a version of overlapping frames.

12. The system of claim 10 wherein the neural network has multiple convolutional units to decrease the resolution of time samples represented while maintaining a representation of a same number of frequency channels throughout the neural network.

13. The system of claim 10 wherein the neural network has a plurality of convolutional units each having a pointwise convolutional layer.

14. The system of claim 10 wherein the neural network has a plurality of one-dimensional convolutional units each having a convolutional layer arranged to use a one-dimensional kernel that combines a number of time-based values while maintaining an initial number of frequency channels.

15. The system of claim 10 wherein the neural network has a sequence of six convolutional units each with a convolutional layer, wherein the second, third, and fifth convolutional units reduce the sample time or time frame resolution of propagating data at the neural network.

16. The system of claim 10 wherein the generating comprises obtaining angular spectrum phase data from a version of the audio signal data used to form the spike data, and using the phase data to reconstruct the audio signal with the magnitude spectrums.

17. The system of claim 10 wherein the neural network is arranged to receive spike data comprising a sequence of time samples that each show when a spike occurs at a plurality of channels in individual time samples.

18. At least one non-transitory computer readable medium comprising instructions thereon that when executed, cause a computing device to operate by:
receiving audio signal data comprising cochlear-simulating spike data of a plurality of channels provided at each sample of a time sequence of samples;
downsampling the spike data comprising determining a spike group indicator that indicates at least one spike exists for a group of the samples and for individual channels; and
inputting a version of a plurality of the spike group indicators into a spike-to-magnitude encoder to output an audio magnitude spectrum.

19. The medium of claim 18 wherein the downsampling comprises generating a spike group map of spike group indicators that has a time sample resolution reduced from the cochlear-simulating spike data provided by a cochlea model without reducing a number of frequency channels provided by the cochlea model.

20. The medium of claim 19 comprising applying spike grouping to generate a count map of a version of overlapping frames of the spike group indicators, wherein each frame has a count of multiple values of the spike group map from a same channel; and inputting the count map into the encoder.

21. The medium of claim 18 wherein the downsampling comprises moving a summing window to multiple positions over multiple time samples of a single channel to form a spike group indicator each at a different individual window position.

22. At least one non-transitory computer readable medium comprising instructions thereon that when executed, cause a computing device to operate by:
receiving audio signal data comprising cochlear-simulating spike data;
generating a spike group indicator map wherein each location on the map has a spike group indicator that indicates whether or not consecutive time samples of the spike data has at least one spike;
generating counts of the spike group indicators with spikes and within a group of consecutive locations on the spike group indicator map; and inputting the counts into a neural network to output audio magnitude spectrums.

23. The medium of claim 22 comprising using the magnitude spectrums to form a time domain audio signal.

24. The medium of claim 22 wherein the instructions cause the computing device to operate by downsampling the spike data before spike grouping the downsampled spike data.

25. The medium of claim 22 wherein the instructions cause the computing device to operate by applying denoising, dynamic noise suppression, blind source separation, or any combination of these to the reconstructed audio signal before performing audio processing of at least one of: wake-on-voice, keyword spotting, automatic speech recognition, speaker recognition, and angle of arrival detection on the reconstructed audio signal.

* * * * *